US007067714B1

(12) United States Patent  
Ino et al.

(10) Patent No.: US 7,067,714 B1  
(45) Date of Patent: Jun. 27, 2006

(54) N-CALCIUM CHANNEL KNOCKOUT ANIMAL

(75) Inventors: Mitsuhiro Ino, Ushiku (JP); Norimasa Miyamoto, Tsukuba (JP); Eiki Takahashi, Ushiku (JP); Toru Oki, Ushiku (JP); Takashi Yoshinaga, Tsukuba (JP); Shinji Hatakeyama, Ushiku (JP); Tetsuhiro Niidome, Ryugasaki (JP); Kohei Sawada, Kitasoma-gun (JP); Yukio Nishizawa, Tsukuba (JP); Isao Tanaka, Tsukuba (JP)

(73) Assignee: Eisai Research Institute, Tokyo (JP)

( * ) Notice: Subject to any disclaimer, the term of this patent is extended or adjusted under 35 U.S.C. 154(b) by 29 days.

(21) Appl. No.: 10/111,827

(22) PCT Filed: Oct. 26, 2000

(86) PCT No.: PCT/JP00/07503

§ 371 (c)(1),  
(2), (4) Date: Apr. 25, 2002

(87) PCT Pub. No.: WO01/30137

PCT Pub. Date: May 3, 2001

(30) Foreign Application Priority Data

Oct. 26, 1999 (JP) ................................ 11/303809

(51) Int. Cl.  
*G01N 33/00* (2006.01)  
*A01K 67/00* (2006.01)  
*A01K 67/003* (2006.01)  
*A01K 67/027* (2006.01)

(52) U.S. Cl. .............................. 800/18; 800/9; 800/14; 800/3

(58) Field of Classification Search .................... 800/3, 800/8, 21, 9, 14, 18  
See application file for complete search history.

(56) References Cited

U.S. PATENT DOCUMENTS 5,677,288 A    10/1997    Marangos  
6,353,091 B1 *   3/2002    Lipscombe et al. ......... 530/350

FOREIGN PATENT DOCUMENTS

WO    WO 93/04083    3/1993  
WO    WO 99/46383    9/1999

OTHER PUBLICATIONS

Wang L, Bhattacharjee A, Fu J, Li M. Diabetes. Dec. 1996;45(12):abstract, 'Abnormally expressed low-voltage-activated calcium channels in beta-cells from NOD mice and a related clonal cell line'. Wang L, Bhattacharjee A, Fu J, Li M.*

Muth JN, Yamaguchi H, Mikala G, Grupp IL, Lewis W, Cheng H, Song LS, Lakatta EG, Varadi G, Schwartz A. J Biol Chem. Jul. 30, 1999;274(31):21503-6 Cardiac-specific overexpression of the alpha(1) subunit of the L-type voltage-dependent Ca(2+) channel . . .*

Fletcher CF, Copeland NG, Jenkins NA. J Bioenerg Biomembr. Aug. 1998;30(4):abstract, 'Genetic analysis of voltage-depende calcium channels'.*

Saegusa H, Matsuda Y, Tanabe T. Neurosci Res. May 2002;43(1):abstract, 'Effects of ablation of N- and R-type Ca(2+) channels on pain transmission'.*

T. Coppola, et al. Molecular Cloning of a Murine N-type Calcium Channel α1 Subunit; Evidence for Isoforms, Brain Distribution, and Chromosomal Localization. *FEBS Letters*. 338(1994), pp. 1-5.

T. Ishii. "The Effect of Intrathecal Infusion of Cilnidipine, $Ca^{2+}$ Channel Blocker on Neuropathic Pain in Rats." *Kyushu Shika Gakkai Zasshi*, vol. 54(1), 2000, pp. 162-171.

K. Jun, et al. "Ablation of P/Q-type $Ca^{2+}$ Channel Currents, Altered Synaptic Transmission, and Progressive Ataxia in Mice Lacking the $\alpha_{1A}$-subunit." *Proceedings of the National Academy of Sciences USA*, vol. 96(26), Dec. 21, 1999, pp. 15245-15250.

T. Kobayashi. *Clinical Engineering*, vol. 7(12), 1996, pp. 1085-1091.

S. Mansour, et al. "Disruption of the Proto-Oncogene int-2 in Mouse Embryo-derived Stem Cells: A General Strategy for Targeting Mutations to Non-selectable Genes," *Nature*, vol. 336(24), Nov., 1988, pp. 348-352.

Y. Namkung, et al. "Targeted Disruption of the $Ca^{2+}$ channel $\beta_3$ Subunit Reduces N- and L-type $Ca^{2+}$ Channel Activity and Alters the Voltage-dependent Activation of P/Q-type $Ca^{2+}$ Channels in Neurons," *National Academy of Sciences USA*, vol. 95, Sep., 1998, pp. 12010-12015.

J. Nooney, et al. "Identifying Neuronal non-L $Ca^{2+}$ Channels-More Than Stamp Collecting?" *Trend in Pharmacological Sciences*, vol. 18, Oct., 1997, pp. 363-371.

D. Pruneau, et al. ω-Conotoxin GVIA, the N-Type Calcium Channel Inhibitor, is Sympatholytic but not Vagolytic: Consequences for Hemodynamics and Autonomic Reflexes in Conscious Rabbits, *Journal of Cardiovascular Pharmacology*, vol. 16, 1990, pp. 675-680.

(Continued)

*Primary Examiner*—Joseph Woitach  
(74) *Attorney, Agent, or Firm*—Choate, Hall & Stewart, LLP

(57) ABSTRACT

A non-human animal in which a gene coding for the N-type calcium channel is disrupted to lack functional N-type calcium channel, and a method for screening for a substance having a pharmacological action on blood pressure control, transmission of pain, blood sugar level control and so forth by using the animal.

7 Claims, 13 Drawing Sheets

OTHER PUBLICATIONS

H. Saegusa, et al. "Altered Pain Responses in Mice Lacking $\alpha_{1E}$ Subunit of the Voltage-Dependent $Ca^{2+}$ Channel," *Proceedings of the National Academy of Sciences USA*, vol. 97(11), May 23, 2000, pp. 6132-6137.

Z. Wei, et al. "Spinal Morphine/Clonidine Antinociceptive Synergism: Involvement of g Proteins and N-Type Voltage-Dependent Calcium Channels," *Journal of Pharmacology and Experimental Therapeutics*, vol. 278(3), 1996, pp. 1392-1407.

M. Williams, et al. "Structure and Functional Expressionof an ω-Conotoxin-Sensitive Human N-Type Calcium Channel," *Science*, vol. 257, Jul. 17, 1992, pp. 389-395.

Supplementary Partial European Search Report issued Mar. 11, 2003, for pending related Japanese application JP0007503.

* cited by examiner

SEQUENCE LISTING

```
<160> NUMBER OF SEQ ID NOS: 10

<210> SEQ ID NO 1
<211> LENGTH: 7185
<212> TYPE: DNA
<213> ORGANISM: Mus musculus
<220> FEATURE:
<221> NAME/KEY: CDS
<222> LOCATION: (121)..(6984)

<400> SEQUENCE: 1
ggaattcggc tcgagggggcg aggtccaggc agctcgctgc ggctaggcta ggagcccttg      60
gcgcgccgcg ccctcggtgc cgggccgcgg agcccgggat gctcgcggcg cccgggagtc     120 atg gtc cgc ttc ggg gac gag cta ggc ggc cgc tat ggg ggc acc ggc       168
Met Val Arg Phe Gly Asp Glu Leu Gly Gly Arg Tyr Gly Gly Thr Gly
  1               5                  10                  15 ggc ggg gag cgg gct cgg ggc ggc ggg gcc ggc ggg gcg ggt ggc ccg       216
Gly Gly Glu Arg Ala Arg Gly Gly Gly Ala Gly Gly Ala Gly Gly Pro
             20                  25                  30 ggc cag ggg ggt ctg ccg ccg ggc cag cgg gtc ctg tac aag cag tcc       264
Gly Gln Gly Gly Leu Pro Pro Gly Gln Arg Val Leu Tyr Lys Gln Ser
         35                  40                  45 att gcg cag cgc gca cgg act atg gcc ctg tac aac ccc atc cca gtc       312
Ile Ala Gln Arg Ala Arg Thr Met Ala Leu Tyr Asn Pro Ile Pro Val
     50                  55                  60 aag cag aac tgc ttc acc gtc aac cgc tcg ctc ttc gtc ttc agc gag       360
Lys Gln Asn Cys Phe Thr Val Asn Arg Ser Leu Phe Val Phe Ser Glu
 65                  70                  75                  80 gac aac gtc gtc cgc aaa tac gct aag cgc atc acc gaa tgg ccg ccc       408
Asp Asn Val Val Arg Lys Tyr Ala Lys Arg Ile Thr Glu Trp Pro Pro
                 85                  90                  95 ttc gaa tac atg atc ctg gcc acc atc atc gcc aac tgc att gtt ctg       456
```

-continued

```
            Phe Glu Tyr Met Ile Leu Ala Thr Ile Ile Ala Asn Cys Ile Val Leu
                        100                 105                 110 gcc ctg gag cag cac ctc cct gat ggg gac aag act ccc atg tct gag      504
Ala Leu Glu Gln His Leu Pro Asp Gly Asp Lys Thr Pro Met Ser Glu
            115                 120                 125 cga cta gat gac acg gag cct tac ttc atc ggg atc ttt tgc ttt gag      552
Arg Leu Asp Asp Thr Glu Pro Tyr Phe Ile Gly Ile Phe Cys Phe Glu
130                 135                 140 gcg ggc atc aag atc ata gcc ctg ggc ttt gtt ttc cac aag ggc tcc      600
Ala Gly Ile Lys Ile Ile Ala Leu Gly Phe Val Phe His Lys Gly Ser
145                 150                 155                 160 tac ctt cgg aac ggc tgg aat gtc atg gac ttc gtg gtg gta ctc acg      648
Tyr Leu Arg Asn Gly Trp Asn Val Met Asp Phe Val Val Val Leu Thr
                165                 170                 175 ggg att ctc gcc aca gct gga act gac ttt gac ctg cgc aca ctg agg      696
Gly Ile Leu Ala Thr Ala Gly Thr Asp Phe Asp Leu Arg Thr Leu Arg
                180                 185                 190 gct gtg cgt gtg ctt agg ccc ctg aag ctg gtg tct gga att cca agc      744
Ala Val Arg Val Leu Arg Pro Leu Lys Leu Val Ser Gly Ile Pro Ser
            195                 200                 205 ttg cag gtg gtg ctt aag tcc atc atg aag gcc atg gtc ccg ctg ctg      792
Leu Gln Val Val Leu Lys Ser Ile Met Lys Ala Met Val Pro Leu Leu
        210                 215                 220 cag att ggg ctg ctc ctc ttc ttt gcc atc ctc atg ttt ggc atc atc      840
Gln Ile Gly Leu Leu Leu Phe Phe Ala Ile Leu Met Phe Gly Ile Ile
225                 230                 235                 240 ggc ctc gag ttc tat atg ggc aaa ttc cat aag gcc tgt ttc ccc aac      888
Gly Leu Glu Phe Tyr Met Gly Lys Phe His Lys Ala Cys Phe Pro Asn
                245                 250                 255 agc aca gat aca gag cct gtg ggt gac ttt ccc tgt ggc aaa gat ccc      936
Ser Thr Asp Thr Glu Pro Val Gly Asp Phe Pro Cys Gly Lys Asp Pro
                260                 265                 270 cct gct cgt cag tgt gat ggt gac acc gaa tgc cgg gag tac tgg cca      984
Pro Ala Arg Gln Cys Asp Gly Asp Thr Glu Cys Arg Glu Tyr Trp Pro
            275                 280                 285 gga ccc aac ttt ggt atc acc aat ttt gac aac atc ctg ttt gcc atc     1032
Gly Pro Asn Phe Gly Ile Thr Asn Phe Asp Asn Ile Leu Phe Ala Ile
        290                 295                 300 ttg aca gtg ttc cag tgt atc acc atg gag ggc tgg act gac atc ctc     1080
Leu Thr Val Phe Gln Cys Ile Thr Met Glu Gly Trp Thr Asp Ile Leu
305                 310                 315                 320 tac aat aca aat gat gcg gct ggc aac acg tgg aac tgg ttg tac ttc     1128
Tyr Asn Thr Asn Asp Ala Ala Gly Asn Thr Trp Asn Trp Leu Tyr Phe
                325                 330                 335 atc ccc ctc atc atc att ggc tcc ttc ttc atg ctc aac ctg gtg ctg     1176
Ile Pro Leu Ile Ile Ile Gly Ser Phe Phe Met Leu Asn Leu Val Leu
                340                 345                 350 ggt gtg ctt tct gga gag ttt gcc aag gag cgg gag cga gtc gag aac     1224
Gly Val Leu Ser Gly Glu Phe Ala Lys Glu Arg Glu Arg Val Glu Asn
            355                 360                 365 cgc cga gcc ttc ctg aag ctc cgc agg cag cag att gag cga gag         1272
Arg Arg Ala Phe Leu Lys Leu Arg Arg Gln Gln Gln Ile Glu Arg Glu
370                 375                 380 ctg aat ggg tac ttg gag tgg atc ttc aag gca gag gaa gtc atg ttg     1320
Leu Asn Gly Tyr Leu Glu Trp Ile Phe Lys Ala Glu Glu Val Met Leu
385                 390                 395                 400 gca gag gag gac aag aat gca gaa gag aaa tcc cct ttg gat gtg ttg     1368
Ala Glu Glu Asp Lys Asn Ala Glu Glu Lys Ser Pro Leu Asp Val Leu
            405                 410                 415
```

```
aag aga gct gcc acc aag aag agc cga aat gac ctc atc cat gca gaa      1416
Lys Arg Ala Ala Thr Lys Lys Ser Arg Asn Asp Leu Ile His Ala Glu
            420                 425                 430 gag ggg gag gac cgg ttt gta gac ctc tgt gca gtt ggg tct cca ttt      1464
Glu Gly Glu Asp Arg Phe Val Asp Leu Cys Ala Val Gly Ser Pro Phe
        435                 440                 445 gct cgt gcc agc ctc aag agt ggg aag acg gag agc tca tcg tac ttc      1512
Ala Arg Ala Ser Leu Lys Ser Gly Lys Thr Glu Ser Ser Ser Tyr Phe
450                 455                 460 cgg aga aag gag aag atg ttc cgg ttc ttt atc cgg cgt atg gtg aaa      1560
Arg Arg Lys Glu Lys Met Phe Arg Phe Phe Ile Arg Arg Met Val Lys
465                 470                 475                 480 gca cag agc ttc tac tgg gta gta ctg tgt gtg gcc ctg aac aca          1608
Ala Gln Ser Phe Tyr Trp Val Val Leu Cys Val Val Ala Leu Asn Thr
                485                 490                 495 ctg tgt gtg gcc atg gtg cac tat aat cag cct cag cgg ctt acc act      1656
Leu Cys Val Ala Met Val His Tyr Asn Gln Pro Gln Arg Leu Thr Thr
            500                 505                 510 gca ctg tac ttt gca gag ttt gtt ttc ctg ggt ctc ttc ctc aca gag      1704
Ala Leu Tyr Phe Ala Glu Phe Val Phe Leu Gly Leu Phe Leu Thr Glu
        515                 520                 525 atg tcc ctg aag atg tat ggc cta ggg ccc aga agt tac ttc agg tct      1752
Met Ser Leu Lys Met Tyr Gly Leu Gly Pro Arg Ser Tyr Phe Arg Ser
530                 535                 540 tcc ttc aac tgc ttt gac ttt ggg gtg att gtg ggg agt atc ttt gaa      1800
Ser Phe Asn Cys Phe Asp Phe Gly Val Ile Val Gly Ser Ile Phe Glu
545                 550                 555                 560 gta gtc tgg gct gcc atc aag cca gga acc tcc ttt gga atc agt gtg      1848
Val Val Trp Ala Ala Ile Lys Pro Gly Thr Ser Phe Gly Ile Ser Val
                565                 570                 575 ctg cgg gct ctg cga ctg ctg agg ata ttc aaa gtt acc aag tat tgg      1896
Leu Arg Ala Leu Arg Leu Leu Arg Ile Phe Lys Val Thr Lys Tyr Trp
            580                 585                 590 aac tct ctg agg aac ctg gtg gtt tcc ctc ctc aat tcc atg aag tcc      1944
Asn Ser Leu Arg Asn Leu Val Val Ser Leu Leu Asn Ser Met Lys Ser
        595                 600                 605 atc atc agc ctt ctc ttc ctg ctt ttc ctc ttc atc gtg gtc ttc gct      1992
Ile Ile Ser Leu Leu Phe Leu Leu Phe Leu Phe Ile Val Val Phe Ala
610                 615                 620 ctg ttg ggg atg cag ctg ttc gga gga cag ttc aac ttt caa gat gag      2040
Leu Leu Gly Met Gln Leu Phe Gly Gly Gln Phe Asn Phe Gln Asp Glu
625                 630                 635                 640 act cca acc acc att ttt gat acc ttc cca gct gcc atc ctc act gtc      2088
Thr Pro Thr Thr Ile Phe Asp Thr Phe Pro Ala Ala Ile Leu Thr Val
                645                 650                 655 ttt cag atc ctg aca gga gag gat tgg aat gcc gta atg tat cat ggg      2136
Phe Gln Ile Leu Thr Gly Glu Asp Trp Asn Ala Val Met Tyr His Gly
            660                 665                 670 att gag tca caa ggt gga gtc agc aaa ggc atg ttt tct tcc ttt tac      2184
Ile Glu Ser Gln Gly Gly Val Ser Lys Gly Met Phe Ser Ser Phe Tyr
        675                 680                 685 ttc atc gtc ctg aca ctg ttt gga aac tac acc ctg ctg aat gtt ttt      2232
Phe Ile Val Leu Thr Leu Phe Gly Asn Tyr Thr Leu Leu Asn Val Phe
690                 695                 700 ctg gcc att gct gtg gac aac ctt gcc aat gcc cag gag ttg acc aag      2280
Leu Ala Ile Ala Val Asp Asn Leu Ala Asn Ala Gln Glu Leu Thr Lys
705                 710                 715                 720 gat gaa gag gag atg gaa gaa gca gcc aat cag aaa ctt gct ctt cag      2328
Asp Glu Glu Glu Met Glu Glu Ala Ala Asn Gln Lys Leu Ala Leu Gln
                725                 730                 735
```

| | |
|---|---|
| aag gcc aaa gaa gta gct gaa gtc agc ccc atg tct gct gcc aat atc<br>Lys Ala Lys Glu Val Ala Glu Val Ser Pro Met Ser Ala Ala Asn Ile<br>           740                    745                    750 | 2376 |
| tcc atc gct gcg cag gag aac tcg gcc aag gcg cgc tca gta tgg gag<br>Ser Ile Ala Ala Gln Glu Asn Ser Ala Lys Ala Arg Ser Val Trp Glu<br>           755                    760                    765 | 2424 |
| cag cgg gcc agt cag cta agg ctc cag aat ctg cgt gcc agc tgt gag<br>Gln Arg Ala Ser Gln Leu Arg Leu Gln Asn Leu Arg Ala Ser Cys Glu<br>    770                    775                    780 | 2472 |
| gca ttg tac agt gag atg gac cct gag gag cgc ctg cgt tat gcc agc<br>Ala Leu Tyr Ser Glu Met Asp Pro Glu Glu Arg Leu Arg Tyr Ala Ser<br>785                    790                    795                800 | 2520 |
| acg cgc cat gtg agg cca gac atg aag aca cac atg gac cga ccc cta<br>Thr Arg His Val Arg Pro Asp Met Lys Thr His Met Asp Arg Pro Leu<br>                805                    810                    815 | 2568 |
| gtg gtg gag cct ggt cga gat ggc ttg cgg gga ccc gtt ggg agc aag<br>Val Val Glu Pro Gly Arg Asp Gly Leu Arg Gly Pro Val Gly Ser Lys<br>           820                    825                    830 | 2616 |
| tca aag cct gaa ggc acg gag gcc aca gaa agc gcg gac cta cct cgc<br>Ser Lys Pro Glu Gly Thr Glu Ala Thr Glu Ser Ala Asp Leu Pro Arg<br>    835                    840                    845 | 2664 |
| cgg cac cac cgg cat cgt gat agg gac aag acc tca gcc aca gca cct<br>Arg His His Arg His Arg Asp Arg Asp Lys Thr Ser Ala Thr Ala Pro<br>850                    855                    860 | 2712 |
| gct gga ggc gaa cag gac agg aca gaa agc acc gag acc ggg ccc cgg<br>Ala Gly Gly Glu Gln Asp Arg Thr Glu Ser Thr Glu Thr Gly Pro Arg<br>865                    870                    875                880 | 2760 |
| gag gaa cgt gcg cgc cct cgt cga agt cac agc aag gag act cca ggg<br>Glu Glu Arg Ala Arg Pro Arg Arg Ser His Ser Lys Glu Thr Pro Gly<br>                885                    890                    895 | 2808 |
| gct gac acg caa gtg cgc tgt gag cgc agt agg cgt cac cac cgg cgc<br>Ala Asp Thr Gln Val Arg Cys Glu Arg Ser Arg Arg His His Arg Arg<br>           900                    905                    910 | 2856 |
| ggc tcc ccg gag gag gcc act gaa cgg gag cct cgg cgc cac cgt gcc<br>Gly Ser Pro Glu Glu Ala Thr Glu Arg Glu Pro Arg Arg His Arg Ala<br>    915                    920                    925 | 2904 |
| cac cgg cat gca cag gac tca agc aag gag ggc acg gcg ccg gtg ctt<br>His Arg His Ala Gln Asp Ser Ser Lys Glu Gly Thr Ala Pro Val Leu<br>930                    935                    940 | 2952 |
| gta ccc aag ggt gag cga cga gca aga cac cga ggc cca cgc acg ggt<br>Val Pro Lys Gly Glu Arg Arg Ala Arg His Arg Gly Pro Arg Thr Gly<br>945                    950                    955                960 | 3000 |
| cca cgt gag gca gag aac aac gag gag ccc aca cgc agg cac cgt gca<br>Pro Arg Glu Ala Glu Asn Asn Glu Glu Pro Thr Arg Arg His Arg Ala<br>                965                    970                    975 | 3048 |
| agg cat aag gtg cca ccc aca ctg cag ccc cca gag agg gag gct gca<br>Arg His Lys Val Pro Pro Thr Leu Gln Pro Pro Glu Arg Glu Ala Ala<br>           980                    985                    990 | 3096 |
| gag aag gag agc aac gcg gtg gaa ggg gat aag gaa acc cga aat cac<br>Glu Lys Glu Ser Asn Ala Val Glu Gly Asp Lys Glu Thr Arg Asn His<br>    995                    1000                   1005 | 3144 |
| cag ccc aag gaa cct cac tgt gac ctg gag gcc att gca gtt aca ggt<br>Gln Pro Lys Glu Pro His Cys Asp Leu Glu Ala Ile Ala Val Thr Gly<br>  1010                  1015                  1020 | 3192 |
| gtg ggc cct ctg cac atg ctg ccc agc acc tgt ctc cag aaa gtg gac<br>Val Gly Pro Leu His Met Leu Pro Ser Thr Cys Leu Gln Lys Val Asp<br>1025                  1030                  1035                1040 | 3240 |
| gag caa cca gag gat gca gac aac cag cgt aat gtc acc cgg atg ggc<br>Glu Gln Pro Glu Asp Ala Asp Asn Gln Arg Asn Val Thr Arg Met Gly | 3288 |

-continued

|  |  |
|---|---:|
| 1045 1050 1055 | |
| agt cag ccc tca gat ccc agc acc act gtg cat gtc cca gtg aca ctg<br>Ser Gln Pro Ser Asp Pro Ser Thr Thr Val His Val Pro Val Thr Leu<br>1060 1065 1070 | 3336 |
| aca ggc cct cct ggg gag acc cct gta gtt ccc agt ggt aac atg aac<br>Thr Gly Pro Pro Gly Glu Thr Pro Val Val Pro Ser Gly Asn Met Asn<br>1075 1080 1085 | 3384 |
| ctg gaa ggc caa gca gag ggc aag aag gag gca gag gcg gat gat gtg<br>Leu Glu Gly Gln Ala Glu Gly Lys Lys Glu Ala Glu Ala Asp Asp Val<br>1090 1095 1100 | 3432 |
| ctg aga aga ggc ccc agg ccc atc gtt ccc tac agc tcc atg ttt tgt<br>Leu Arg Arg Gly Pro Arg Pro Ile Val Pro Tyr Ser Ser Met Phe Cys<br>1105 1110 1115 1120 | 3480 |
| ctc agc ccc acc aac ctg ttt cgt cgc ttc tgc cat tac att gtg acc<br>Leu Ser Pro Thr Asn Leu Phe Arg Arg Phe Cys His Tyr Ile Val Thr<br>1125 1130 1135 | 3528 |
| atg cgg tac ttg gag atg gta att ctt gtg gtc att gcc ttg agc agc<br>Met Arg Tyr Leu Glu Met Val Ile Leu Val Val Ile Ala Leu Ser Ser<br>1140 1145 1150 | 3576 |
| att gcc ctg gct gca gag gat cct gtg cgg aca gat tca ttc agg aac<br>Ile Ala Leu Ala Ala Glu Asp Pro Val Arg Thr Asp Ser Phe Arg Asn<br>1155 1160 1165 | 3624 |
| aac gct tta gag tac atg gat tac atc ttt aca gga gtc ttc acc tgt<br>Asn Ala Leu Glu Tyr Met Asp Tyr Ile Phe Thr Gly Val Phe Thr Cys<br>1170 1175 1180 | 3672 |
| gaa atg gtc ata aag atg ata gac ttg ggc ttg ctg ctg cac cct ggt<br>Glu Met Val Ile Lys Met Ile Asp Leu Gly Leu Leu Leu His Pro Gly<br>1185 1190 1195 1200 | 3720 |
| gcc tac ttc cgg gac ctg tgg aac att ctg gac ttc atc gtt gtc agt<br>Ala Tyr Phe Arg Asp Leu Trp Asn Ile Leu Asp Phe Ile Val Val Ser<br>1205 1210 1215 | 3768 |
| gga gcc ctg gtg gca ttt gcg ttc tca gga tcc aaa ggg aaa gac atc<br>Gly Ala Leu Val Ala Phe Ala Phe Ser Gly Ser Lys Gly Lys Asp Ile<br>1220 1225 1230 | 3816 |
| aat acc atc aag tct ctg aga gtc ctg cgt gtc ctg agg ccc ctc aag<br>Asn Thr Ile Lys Ser Leu Arg Val Leu Arg Val Leu Arg Pro Leu Lys<br>1235 1240 1245 | 3864 |
| acc atc aag cgg ctg cct aaa ctc aag gct gtc ttt gac tgt gtg gtg<br>Thr Ile Lys Arg Leu Pro Lys Leu Lys Ala Val Phe Asp Cys Val Val<br>1250 1255 1260 | 3912 |
| aac tcc ctg aag aac gtc ttg aac atc ctg att gtc tac atg ctc ttc<br>Asn Ser Leu Lys Asn Val Leu Asn Ile Leu Ile Val Tyr Met Leu Phe<br>1265 1270 1275 1280 | 3960 |
| atg ttc ata ttt gcc gtc att gcc gtc cag ctc ttc aaa ggg aag ttc<br>Met Phe Ile Phe Ala Val Ile Ala Val Gln Leu Phe Lys Gly Lys Phe<br>1285 1290 1295 | 4008 |
| ttt tac tgt act gat gaa tcc aag gag ctg gag agg gac tgc cgg ggt<br>Phe Tyr Cys Thr Asp Glu Ser Lys Glu Leu Glu Arg Asp Cys Arg Gly<br>1300 1305 1310 | 4056 |
| cag tat ttg gat tat gag aag gaa gaa gta gaa gcc cag cca agg cag<br>Gln Tyr Leu Asp Tyr Glu Lys Glu Glu Val Glu Ala Gln Pro Arg Gln<br>1315 1320 1325 | 4104 |
| tgg aag aaa tat gac ttc cac tat gac aat gtt ctc tgg gcc ttg ttg<br>Trp Lys Lys Tyr Asp Phe His Tyr Asp Asn Val Leu Trp Ala Leu Leu<br>1330 1335 1340 | 4152 |
| acg ctg ttc aca gtg tcc acg gga gag ggg tgg ccc atg gtg ctg aaa<br>Thr Leu Phe Thr Val Ser Thr Gly Glu Gly Trp Pro Met Val Leu Lys<br>1345 1350 1355 1360 | 4200 |
| cac tct gtg gat gcc acc tat gag gaa cag ggg ccc agt ccc ggc ttc | 4248 |

-continued

```
His Ser Val Asp Ala Thr Tyr Glu Glu Gln Gly Pro Ser Pro Gly Phe
            1365                1370                1375 cgg atg gag ctc tcc atc ctc tac gtg gtc tac ttt gtg gtc ttc cct         4296
Arg Met Glu Leu Ser Ile Leu Tyr Val Val Tyr Phe Val Val Phe Pro
1380                1385                1390 ttt ttc ttt gtc aac atc ttt gtg gcc ttg atc att atc acc ttc cag         4344
Phe Phe Phe Val Asn Ile Phe Val Ala Leu Ile Ile Ile Thr Phe Gln
        1395                1400                1405 gaa cag gga gat aag gtg atg tct gaa tgc agc tta gaa aag aat gag         4392
Glu Gln Gly Asp Lys Val Met Ser Glu Cys Ser Leu Glu Lys Asn Glu
    1410                1415                1420 agg gct tgc att gat ttt gcc atc agt gcc aag ccc ctg aca cgg tac         4440
Arg Ala Cys Ile Asp Phe Ala Ile Ser Ala Lys Pro Leu Thr Arg Tyr
1425                1430                1435                1440 atg cct caa aac aaa cag tcg ttc cag tat aag aca tgg aca ttc gtg         4488
Met Pro Gln Asn Lys Gln Ser Phe Gln Tyr Lys Thr Trp Thr Phe Val
                1445                1450                1455 gtc tct cca ccc ttt gag tac ttc atc atg gct atg ata gcc ctc aac         4536
Val Ser Pro Pro Phe Glu Tyr Phe Ile Met Ala Met Ile Ala Leu Asn
            1460                1465                1470 aca gtg gtg ctg atg atg aag ttc tat gat gca cct tat gag tac gag         4584
Thr Val Val Leu Met Met Lys Phe Tyr Asp Ala Pro Tyr Glu Tyr Glu
        1475                1480                1485 ctg atg ctg aaa tgc ctg aac att gtc ttc aca tcc atg ttc tcg atg         4632
Leu Met Leu Lys Cys Leu Asn Ile Val Phe Thr Ser Met Phe Ser Met
    1490                1495                1500 gag tgc ata ctg aag atc atc gcc ttt ggg gta ttg aac tac ttc aga         4680
Glu Cys Ile Leu Lys Ile Ile Ala Phe Gly Val Leu Asn Tyr Phe Arg
1505                1510                1515                1520 gat gcc tgg aat gtc ttt gac ttt gtc acg gtt ttg gga agt att act         4728
Asp Ala Trp Asn Val Phe Asp Phe Val Thr Val Leu Gly Ser Ile Thr
                1525                1530                1535 gat att tta gta aca gag att gcg gaa acg aac aac ttc atc aac cta         4776
Asp Ile Leu Val Thr Glu Ile Ala Glu Thr Asn Asn Phe Ile Asn Leu
            1540                1545                1550 agc ttc ctt cgc ctc ttc cgg gcg gca cgg ctg atc aag ctg ctt cgc         4824
Ser Phe Leu Arg Leu Phe Arg Ala Ala Arg Leu Ile Lys Leu Leu Arg
        1555                1560                1565 cag ggc tac acc atc cgc atc cta ttg tgg acc ttc gtc cag tcc ttt         4872
Gln Gly Tyr Thr Ile Arg Ile Leu Leu Trp Thr Phe Val Gln Ser Phe
    1570                1575                1580 aag gcg ctg ccc tac gtg tgc ctc ctc att gcc atg ctg ttc ttc atc         4920
Lys Ala Leu Pro Tyr Val Cys Leu Leu Ile Ala Met Leu Phe Phe Ile
1585                1590                1595                1600 tac gcc atc atc gga atg cag gtt ttt gga aac agt gcc ctt gat gat         4968
Tyr Ala Ile Ile Gly Met Gln Val Phe Gly Asn Ser Ala Leu Asp Asp
                1605                1610                1615 gac acc agt atc aac cga cac aac aac ttc cgg aca ttt ctg caa gcc         5016
Asp Thr Ser Ile Asn Arg His Asn Asn Phe Arg Thr Phe Leu Gln Ala
            1620                1625                1630 ata atg cta ttg ttc agg agt gcc act ggg gag gcc tgg cat gag atc         5064
Ile Met Leu Leu Phe Arg Ser Ala Thr Gly Glu Ala Trp His Glu Ile
        1635                1640                1645 atg ctg tca tgt ctg gac aac cgg gcc tgt gac cca cat gcc aac gcc         5112
Met Leu Ser Cys Leu Asp Asn Arg Ala Cys Asp Pro His Ala Asn Ala
    1650                1655                1660 agt gag tgc ggg agc gac ttt gcc tat ttt tat ttt gtc tcc ttc atc         5160
Ser Glu Cys Gly Ser Asp Phe Ala Tyr Phe Tyr Phe Val Ser Phe Ile
1665                1670                1675                1680
```

```
ttc ctc tgt tcc ttt ctg atg ttg aac ctc ttt gtt gct gta atc atg       5208
Phe Leu Cys Ser Phe Leu Met Leu Asn Leu Phe Val Ala Val Ile Met
            1685                1690                1695 gac aat ttt gag tac ctc act cgg gac tct tcc atc cta ggg cct cac       5256
Asp Asn Phe Glu Tyr Leu Thr Arg Asp Ser Ser Ile Leu Gly Pro His
        1700                1705                1710 cac tta gac gaa ttc att cga gtc tgg gct gaa tac gac cca gct gcg       5304
His Leu Asp Glu Phe Ile Arg Val Trp Ala Glu Tyr Asp Pro Ala Ala
    1715                1720                1725 tgt ggg cgc atc agt tac aat gac atg ttt gag atg ctg aaa cac atg       5352
Cys Gly Arg Ile Ser Tyr Asn Asp Met Phe Glu Met Leu Lys His Met
1730                1735                1740 tcc cca cct ctg ggg ttg ggg aag aaa tgc ccg gct cga gtt gca tac       5400
Ser Pro Pro Leu Gly Leu Gly Lys Lys Cys Pro Ala Arg Val Ala Tyr
            1745                1750                1755                1760 aag cgc ctg gtt cgc atg aac atg ccc ata tcc aat gag gac atg acg       5448
Lys Arg Leu Val Arg Met Asn Met Pro Ile Ser Asn Glu Asp Met Thr
        1765                1770                1775 gtg cac ttt acg tcc aca ctg atg gcc ctc atc cgg aca gca ctg gag       5496
Val His Phe Thr Ser Thr Leu Met Ala Leu Ile Arg Thr Ala Leu Glu
    1780                1785                1790 atc aag ctt gcc cca gct gac gag atg aca gtg ggg aag gtc tat gct       5544
Ile Lys Leu Ala Pro Ala Asp Glu Met Thr Val Gly Lys Val Tyr Ala
1795                1800                1805 gct ctc atg ata ttt gac ttc tac aaa cag aac aaa acc acc aga gat       5592
Ala Leu Met Ile Phe Asp Phe Tyr Lys Gln Asn Lys Thr Thr Arg Asp
            1810                1815                1820 cag act cac caa gct ccc gga ggc ctg tcc cag atg ggt ccc gtt tcc       5640
Gln Thr His Gln Ala Pro Gly Gly Leu Ser Gln Met Gly Pro Val Ser
1825                1830                1835                1840 ctg ttc cac cct ctg aag gcc acc ctg gaa cag aca cag ccc gct gtg       5688
Leu Phe His Pro Leu Lys Ala Thr Leu Glu Gln Thr Gln Pro Ala Val
        1845                1850                1855 ctt cga gga gct cgg gtt ttc ctt cgg caa aag agt gca act tcc ctc       5736
Leu Arg Gly Ala Arg Val Phe Leu Arg Gln Lys Ser Ala Thr Ser Leu
    1860                1865                1870 agc aat ggg ggt gcc ata caa acc cag gaa agt gga tca agg agt cgc       5784
Ser Asn Gly Gly Ala Ile Gln Thr Gln Glu Ser Gly Ser Arg Ser Arg
1875                1880                1885 tgt cct ggg gga cgc aga ggg acc caa gat gca ctt tat gag ggc aga       5832
Cys Pro Gly Gly Arg Arg Gly Thr Gln Asp Ala Leu Tyr Glu Gly Arg
        1890                1895                1900 gca cct cta gaa cgt gac cat tct aaa gag atc cct gtg ggg cag tca       5880
Ala Pro Leu Glu Arg Asp His Ser Lys Glu Ile Pro Val Gly Gln Ser
1905                1910                1915                1920 gga aca ctg ctg gtg gat gtc cag atg cag aac atg aca ctg aga gga       5928
Gly Thr Leu Leu Val Asp Val Gln Met Gln Asn Met Thr Leu Arg Gly
            1925                1930                1935 cca gat ggg gat ccc cag cct ggc ctg gaa agc caa ggc aga gct gcc       5976
Pro Asp Gly Asp Pro Gln Pro Gly Leu Glu Ser Gln Gly Arg Ala Ala
        1940                1945                1950 tct atg cta cgc cta gcg gca gaa aca cag ccg gcc cct aat gcc agc       6024
Ser Met Leu Arg Leu Ala Ala Glu Thr Gln Pro Ala Pro Asn Ala Ser
    1955                1960                1965 ccc atg aag cgc tcc atc tcc aca ctg gct cca cgc cca gat ggg act       6072
Pro Met Lys Arg Ser Ile Ser Thr Leu Ala Pro Arg Pro Asp Gly Thr
1970                1975                1980 cag ctt tgc agc aca gtt ctg gac cgg cct cct cct agc cag gca tca       6120
Gln Leu Cys Ser Thr Val Leu Asp Arg Pro Pro Pro Ser Gln Ala Ser
1985                1990                1995                2000
```

```
cat cac cac cac cac cgc tgc cac cgg cgc aga gac aag aag caa agg      6168
His His His His His Arg Cys His Arg Arg Arg Asp Lys Lys Gln Arg
                2005                2010                2015 tcc ctg gaa aag ggg ccc agc ctg tct gtt gac cca gaa ggt gca cca      6216
Ser Leu Glu Lys Gly Pro Ser Leu Ser Val Asp Pro Glu Gly Ala Pro
                2020                2025                2030 agc act gct gct gca gga cct ggt ctg ccc cat gga gaa gga tcc acc      6264
Ser Thr Ala Ala Ala Gly Pro Gly Leu Pro His Gly Glu Gly Ser Thr
                2035                2040                2045 gcc tgc cgg cgg gac cgt aaa cag gag cga ggc cgg tcc cag gag cgg      6312
Ala Cys Arg Arg Asp Arg Lys Gln Glu Arg Gly Arg Ser Gln Glu Arg
                2050                2055                2060 agg cag ccc tca tct tcc tct tca gag aag cag cgc ttc tat tcc tgt      6360
Arg Gln Pro Ser Ser Ser Ser Ser Glu Lys Gln Arg Phe Tyr Ser Cys
2065                2070                2075                2080 gac cgc ttg gga gcc ggg agc ccc caa ctg atg ccc tca ctc agt agc      6408
Asp Arg Leu Gly Ala Gly Ser Pro Gln Leu Met Pro Ser Leu Ser Ser
                2085                2090                2095 cac ccc aca tcg ccg gcg gcg gcg cta gag cca gca ccc cac cca cag      6456
His Pro Thr Ser Pro Ala Ala Ala Leu Glu Pro Ala Pro His Pro Gln
                2100                2105                2110 ggc agt ggt tcc gtt aat ggg agc ccc ttg atg tca aca tcc ggt gct      6504
Gly Ser Gly Ser Val Asn Gly Ser Pro Leu Met Ser Thr Ser Gly Ala
                2115                2120                2125 att act ccc ggg cga ggt ggg cgg agg cag ctc ccc cag act cct ctg      6552
Ile Thr Pro Gly Arg Gly Gly Arg Arg Gln Leu Pro Gln Thr Pro Leu
                2130                2135                2140 acc cca cgc ccc agc atc acc tac aag acc gcc aat tcc tcg cct gtc      6600
Thr Pro Arg Pro Ser Ile Thr Tyr Lys Thr Ala Asn Ser Ser Pro Val
2145                2150                2155                2160 cac ttt gct gag ggt cag agc ggc ctc cca gcc ttc tcc cct ggc cgt      6648
His Phe Ala Glu Gly Gln Ser Gly Leu Pro Ala Phe Ser Pro Gly Arg
                2165                2170                2175 ctc agc cgc ggc ctt tct gaa cac aat gcc ctg ctc cag aaa gag ccc      6696
Leu Ser Arg Gly Leu Ser Glu His Asn Ala Leu Leu Gln Lys Glu Pro
                2180                2185                2190 ctg agc cag cct cta gct cct ggc tcc cga att ggc tct gac cct tac      6744
Leu Ser Gln Pro Leu Ala Pro Gly Ser Arg Ile Gly Ser Asp Pro Tyr
                2195                2200                2205 cta ggg cag cgt ctg gac agt gag gcc tcc gcc cac acc ctg cct gag      6792
Leu Gly Gln Arg Leu Asp Ser Glu Ala Ser Ala His Thr Leu Pro Glu
                2210                2215                2220 gat aca ctc acc ttt gaa gag gca gtg gcc acc aac tct ggc cgc tcc      6840
Asp Thr Leu Thr Phe Glu Glu Ala Val Ala Thr Asn Ser Gly Arg Ser
2225                2230                2235                2240 tcc agg act tcc tat gtg tcc tcc ctc act tcc caa tcc cac cct ctc      6888
Ser Arg Thr Ser Tyr Val Ser Ser Leu Thr Ser Gln Ser His Pro Leu
                2245                2250                2255 cgc cgt gta ccc aat ggc tat cac tgc act ttg gga ctc aac act ggc      6936
Arg Arg Val Pro Asn Gly Tyr His Cys Thr Leu Gly Leu Asn Thr Gly
                2260                2265                2270 gtc ggg gca cga gca agc tac cac cac ccc gat cag gac cac tgg tgc      6984
Val Gly Ala Arg Ala Ser Tyr His His Pro Asp Gln Asp His Trp Cys
                2275                2280                2285 tagcttcacc acgaccaccc atgtaccagc tccatgggtg agggttccag ttgatgagtt      7044
ttatcatccc actctggact gtggggtcac aaccctggga ggagggccct cacatctcgg      7104
cctctgtggt ggaggctcct gcttccctcc ctccctccct ttttacactg gatagactaa      7164
``` taaagcccctt tcttagaggg g                                                7185

<210> SEQ ID NO 2
<211> LENGTH: 2288
<212> TYPE: PRT
<213> ORGANISM: Mus musculus

<400> SEQUENCE: 2

Met Val Arg Phe Gly Asp Glu Leu Gly Gly Arg Tyr Gly Gly Thr Gly
1               5                   10                  15

Gly Gly Glu Arg Ala Arg Gly Gly Ala Gly Gly Ala Gly Gly Pro
        20                  25                  30

Gly Gln Gly Gly Leu Pro Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
                100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                165                 170                 175

Gly Ile Leu Ala Thr Ala Gly Thr Asp Phe Asp Leu Arg Thr Leu Arg
                180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Gly Ile Ile
225                 230                 235                 240

Gly Leu Glu Phe Tyr Met Gly Lys Phe His Lys Ala Cys Phe Pro Asn
                245                 250                 255

Ser Thr Asp Thr Glu Pro Val Gly Asp Phe Pro Cys Gly Lys Asp Pro
                260                 265                 270

Pro Ala Arg Gln Cys Asp Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
        290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
                340                 345                 350

Gly Val Leu Ser Gly Glu Phe Ala Lys Glu Arg Glu Arg Val Glu Asn
        355                 360                 365

```
Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                     390                 395                 400

Ala Glu Glu Asp Lys Asn Ala Glu Glu Lys Ser Pro Leu Asp Val Leu
                405                 410                 415

Lys Arg Ala Ala Thr Lys Lys Ser Arg Asn Asp Leu Ile His Ala Glu
                420                 425                 430

Glu Gly Glu Asp Arg Phe Val Asp Leu Cys Ala Val Gly Ser Pro Phe
            435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Gln Arg Leu Thr Thr
            500                 505                 510

Ala Leu Tyr Phe Ala Glu Phe Val Phe Leu Gly Leu Phe Leu Thr Glu
    515                 520                 525

Met Ser Leu Lys Met Tyr Gly Leu Gly Pro Arg Ser Tyr Phe Arg Ser
530                 535                 540

Ser Phe Asn Cys Phe Asp Phe Gly Val Ile Val Gly Ser Ile Phe Glu
545                 550                 555                 560

Val Val Trp Ala Ala Ile Lys Pro Gly Thr Ser Phe Gly Ile Ser Val
                565                 570                 575

Leu Arg Ala Leu Arg Leu Leu Arg Ile Phe Lys Val Thr Lys Tyr Trp
            580                 585                 590

Asn Ser Leu Arg Asn Leu Val Val Ser Leu Leu Asn Ser Met Lys Ser
            595                 600                 605

Ile Ile Ser Leu Leu Phe Leu Leu Phe Leu Phe Ile Val Val Phe Ala
610                 615                 620

Leu Leu Gly Met Gln Leu Phe Gly Gly Gln Phe Asn Phe Gln Asp Glu
625                 630                 635                 640

Thr Pro Thr Thr Ile Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Gln Glu Asn Ser Ala Lys Ala Arg Ser Val Trp Glu
        755                 760                 765

Gln Arg Ala Ser Gln Leu Arg Leu Gln Asn Leu Arg Ala Ser Cys Glu
    770                 775                 780

Ala Leu Tyr Ser Glu Met Asp Pro Glu Glu Arg Leu Arg Tyr Ala Ser
```

-continued

```
              785                 790                 795                 800
Thr Arg His Val Arg Pro Asp Met Lys Thr His Met Asp Arg Pro Leu
                        805                 810                 815
Val Val Glu Pro Gly Arg Asp Gly Leu Arg Gly Pro Val Gly Ser Lys
                820                 825                 830
Ser Lys Pro Glu Gly Thr Glu Ala Thr Glu Ser Ala Asp Leu Pro Arg
            835                 840                 845
Arg His His Arg His Arg Asp Arg Asp Lys Thr Ser Ala Thr Ala Pro
        850                 855                 860
Ala Gly Gly Glu Gln Asp Arg Thr Glu Ser Thr Glu Thr Gly Pro Arg
865                 870                 875                 880
Glu Glu Arg Ala Arg Pro Arg Arg Ser His Ser Lys Glu Thr Pro Gly
                    885                 890                 895
Ala Asp Thr Gln Val Arg Cys Glu Arg Ser Arg Arg His His Arg Arg
                900                 905                 910
Gly Ser Pro Glu Glu Ala Thr Glu Arg Glu Pro Arg Arg His Arg Ala
            915                 920                 925
His Arg His Ala Gln Asp Ser Ser Lys Glu Gly Thr Ala Pro Val Leu
        930                 935                 940
Val Pro Lys Gly Glu Arg Arg Ala Arg His Arg Gly Pro Arg Thr Gly
945                 950                 955                 960
Pro Arg Glu Ala Glu Asn Asn Glu Glu Pro Thr Arg Arg His Arg Ala
                    965                 970                 975
Arg His Lys Val Pro Pro Thr Leu Gln Pro Pro Glu Arg Glu Ala Ala
                980                 985                 990
Glu Lys Glu Ser Asn Ala Val Glu Gly Asp Lys Glu Thr Arg Asn His
            995                 1000                1005
Gln Pro Lys Glu Pro His Cys Asp Leu Glu Ala Ile Ala Val Thr Gly
        1010                1015                1020
Val Gly Pro Leu His Met Leu Pro Ser Thr Cys Leu Gln Lys Val Asp
1025                1030                1035                1040
Glu Gln Pro Glu Asp Ala Asp Asn Gln Arg Asn Val Thr Arg Met Gly
                    1045                1050                1055
Ser Gln Pro Ser Asp Pro Ser Thr Thr Val His Val Pro Val Thr Leu
                1060                1065                1070
Thr Gly Pro Pro Gly Glu Thr Pro Val Val Pro Ser Gly Asn Met Asn
            1075                1080                1085
Leu Glu Gly Gln Ala Glu Gly Lys Lys Glu Ala Glu Ala Asp Asp Val
        1090                1095                1100
Leu Arg Arg Gly Pro Arg Pro Ile Val Pro Tyr Ser Ser Met Phe Cys
1105                1110                1115                1120
Leu Ser Pro Thr Asn Leu Phe Arg Arg Phe Cys His Tyr Ile Val Thr
                    1125                1130                1135
Met Arg Tyr Leu Glu Met Val Ile Leu Val Val Ile Ala Leu Ser Ser
                1140                1145                1150
Ile Ala Leu Ala Ala Glu Asp Pro Val Arg Thr Asp Ser Phe Arg Asn
            1155                1160                1165
Asn Ala Leu Glu Tyr Met Asp Tyr Ile Phe Thr Gly Val Phe Thr Cys
        1170                1175                1180
Glu Met Val Ile Lys Met Ile Asp Leu Gly Leu Leu Leu His Pro Gly
1185                1190                1195                1200
Ala Tyr Phe Arg Asp Leu Trp Asn Ile Leu Asp Phe Ile Val Val Ser
                    1205                1210                1215
```

-continued

Gly Ala Leu Val Ala Phe Ala Phe Ser Gly Ser Lys Gly Lys Asp Ile
        1220                1225                1230

Asn Thr Ile Lys Ser Leu Arg Val Leu Arg Val Leu Arg Pro Leu Lys
    1235                1240                1245

Thr Ile Lys Arg Leu Pro Lys Leu Lys Ala Val Phe Asp Cys Val Val
    1250                1255                1260

Asn Ser Leu Lys Asn Val Leu Asn Ile Leu Ile Val Tyr Met Leu Phe
1265                1270                1275                1280

Met Phe Ile Phe Ala Val Ile Ala Val Gln Leu Phe Lys Gly Lys Phe
            1285                1290                1295

Phe Tyr Cys Thr Asp Glu Ser Lys Glu Leu Glu Arg Asp Cys Arg Gly
        1300                1305                1310

Gln Tyr Leu Asp Tyr Glu Lys Glu Glu Val Glu Ala Gln Pro Arg Gln
        1315                1320                1325

Trp Lys Lys Tyr Asp Phe His Tyr Asp Asn Val Leu Trp Ala Leu Leu
    1330                1335                1340

Thr Leu Phe Thr Val Ser Thr Gly Glu Gly Trp Pro Met Val Leu Lys
1345                1350                1355                1360

His Ser Val Asp Ala Thr Tyr Glu Glu Gln Gly Pro Ser Pro Gly Phe
            1365                1370                1375

Arg Met Glu Leu Ser Ile Leu Tyr Val Val Tyr Phe Val Val Phe Pro
        1380                1385                1390

Phe Phe Phe Val Asn Ile Phe Val Ala Leu Ile Ile Ile Thr Phe Gln
        1395                1400                1405

Glu Gln Gly Asp Lys Val Met Ser Glu Cys Ser Leu Glu Lys Asn Glu
    1410                1415                1420

Arg Ala Cys Ile Asp Phe Ala Ile Ser Ala Lys Pro Leu Thr Arg Tyr
1425                1430                1435                1440

Met Pro Gln Asn Lys Gln Ser Phe Gln Tyr Lys Thr Trp Thr Phe Val
            1445                1450                1455

Val Ser Pro Pro Phe Glu Tyr Phe Ile Met Ala Met Ile Ala Leu Asn
        1460                1465                1470

Thr Val Val Leu Met Met Lys Phe Tyr Asp Ala Pro Tyr Glu Tyr Glu
    1475                1480                1485

Leu Met Leu Lys Cys Leu Asn Ile Val Phe Thr Ser Met Phe Ser Met
    1490                1495                1500

Glu Cys Ile Leu Lys Ile Ile Ala Phe Gly Val Leu Asn Tyr Phe Arg
1505                1510                1515                1520

Asp Ala Trp Asn Val Phe Asp Phe Val Thr Val Leu Gly Ser Ile Thr
            1525                1530                1535

Asp Ile Leu Val Thr Glu Ile Ala Glu Thr Asn Asn Phe Ile Asn Leu
        1540                1545                1550

Ser Phe Leu Arg Leu Phe Arg Ala Ala Arg Leu Ile Lys Leu Leu Arg
    1555                1560                1565

Gln Gly Tyr Thr Ile Arg Ile Leu Leu Trp Thr Phe Val Gln Ser Phe
    1570                1575                1580

Lys Ala Leu Pro Tyr Val Cys Leu Leu Ile Ala Met Leu Phe Phe Ile
1585                1590                1595                1600

Tyr Ala Ile Ile Gly Met Gln Val Phe Gly Asn Ser Ala Leu Asp Asp
            1605                1610                1615

Asp Thr Ser Ile Asn Arg His Asn Asn Phe Arg Thr Phe Leu Gln Ala
        1620                1625                1630

-continued

Ile Met Leu Leu Phe Arg Ser Ala Thr Gly Glu Ala Trp His Glu Ile
   1635                1640                1645

Met Leu Ser Cys Leu Asp Asn Arg Ala Cys Asp Pro His Ala Asn Ala
1650                1655                1660

Ser Glu Cys Gly Ser Asp Phe Ala Tyr Phe Tyr Phe Val Ser Phe Ile
1665                1670                1675                1680

Phe Leu Cys Ser Phe Leu Met Leu Asn Leu Phe Val Ala Val Ile Met
               1685                1690                1695

Asp Asn Phe Glu Tyr Leu Thr Arg Asp Ser Ser Ile Leu Gly Pro His
               1700                1705                1710

His Leu Asp Glu Phe Ile Arg Val Trp Ala Glu Tyr Asp Pro Ala Ala
   1715                1720                1725

Cys Gly Arg Ile Ser Tyr Asn Asp Met Phe Glu Met Leu Lys His Met
   1730                1735                1740

Ser Pro Pro Leu Gly Leu Gly Lys Lys Cys Pro Ala Arg Val Ala Tyr
1745                1750                1755                1760

Lys Arg Leu Val Arg Met Asn Met Pro Ile Ser Asn Glu Asp Met Thr
               1765                1770                1775

Val His Phe Thr Ser Thr Leu Met Ala Leu Ile Arg Thr Ala Leu Glu
               1780                1785                1790

Ile Lys Leu Ala Pro Ala Asp Glu Met Thr Val Gly Lys Val Tyr Ala
   1795                1800                1805

Ala Leu Met Ile Phe Asp Phe Tyr Lys Gln Asn Lys Thr Thr Arg Asp
   1810                1815                1820

Gln Thr His Gln Ala Pro Gly Gly Leu Ser Gln Met Gly Pro Val Ser
1825                1830                1835                1840

Leu Phe His Pro Leu Lys Ala Thr Leu Glu Gln Thr Gln Pro Ala Val
               1845                1850                1855

Leu Arg Gly Ala Arg Val Phe Leu Arg Gln Lys Ser Ala Thr Ser Leu
               1860                1865                1870

Ser Asn Gly Gly Ala Ile Gln Thr Gln Glu Ser Gly Ser Arg Ser Arg
   1875                1880                1885

Cys Pro Gly Gly Arg Arg Gly Thr Gln Asp Ala Leu Tyr Glu Gly Arg
   1890                1895                1900

Ala Pro Leu Glu Arg Asp His Ser Lys Glu Ile Pro Val Gly Gln Ser
1905                1910                1915                1920

Gly Thr Leu Leu Val Asp Val Gln Met Gln Asn Met Thr Leu Arg Gly
               1925                1930                1935

Pro Asp Gly Asp Pro Gln Pro Gly Leu Glu Ser Gln Gly Arg Ala Ala
               1940                1945                1950

Ser Met Leu Arg Leu Ala Ala Glu Thr Gln Pro Ala Pro Asn Ala Ser
   1955                1960                1965

Pro Met Lys Arg Ser Ile Ser Thr Leu Ala Pro Arg Pro Asp Gly Thr
   1970                1975                1980

Gln Leu Cys Ser Thr Val Leu Asp Arg Pro Pro Ser Gln Ala Ser
1985                1990                1995                2000

His His His His His Arg Cys His Arg Arg Asp Lys Lys Gln Arg
               2005                2010                2015

Ser Leu Glu Lys Gly Pro Ser Leu Ser Val Asp Pro Glu Gly Ala Pro
               2020                2025                2030

Ser Thr Ala Ala Ala Gly Pro Gly Leu Pro His Gly Glu Gly Ser Thr
               2035                2040                2045

Ala Cys Arg Arg Asp Arg Lys Gln Glu Arg Gly Arg Ser Gln Glu Arg

-continued

```
                 2050                2055                2060
Arg Gln Pro Ser Ser Ser Ser Glu Lys Gln Arg Phe Tyr Ser Cys
            2065                2070                2075                2080

Asp Arg Leu Gly Ala Gly Ser Pro Gln Leu Met Pro Ser Leu Ser Ser
                 2085                2090                2095

His Pro Thr Ser Pro Ala Ala Ala Leu Glu Pro Ala His Pro Gln
            2100                2105                2110

Gly Ser Gly Ser Val Asn Gly Ser Pro Leu Met Ser Thr Ser Gly Ala
                 2115                2120                2125

Ile Thr Pro Gly Arg Gly Gly Arg Gln Leu Pro Gln Thr Pro Leu
            2130                2135                2140

Thr Pro Arg Pro Ser Ile Thr Tyr Lys Thr Ala Asn Ser Ser Pro Val
2145                2150                2155                2160

His Phe Ala Glu Gly Gln Ser Gly Leu Pro Ala Phe Ser Pro Gly Arg
                 2165                2170                2175

Leu Ser Arg Gly Leu Ser Glu His Asn Ala Leu Leu Gln Lys Glu Pro
            2180                2185                2190

Leu Ser Gln Pro Leu Ala Pro Gly Ser Arg Ile Gly Ser Asp Pro Tyr
            2195                2200                2205

Leu Gly Gln Arg Leu Asp Ser Glu Ala Ser Ala His Thr Leu Pro Glu
            2210                2215                2220

Asp Thr Leu Thr Phe Glu Glu Ala Val Ala Thr Asn Ser Gly Arg Ser
2225                2230                2235                2240

Ser Arg Thr Ser Tyr Val Ser Ser Leu Thr Ser Gln Ser His Pro Leu
            2245                2250                2255

Arg Arg Val Pro Asn Gly Tyr His Cys Thr Leu Gly Leu Asn Thr Gly
            2260                2265                2270

Val Gly Ala Arg Ala Ser Tyr His His Pro Asp Gln Asp His Trp Cys
            2275                2280                2285

<210> SEQ ID NO 3
<211> LENGTH: 27
<212> TYPE: PRT
<213> ORGANISM: Conus geographus
<220> FEATURE:
<221> NAME/KEY: MOD_RES
<222> LOCATION: 4, 10, 21
<223> OTHER INFORMATION: Xaa=hydroxyproline

<400> SEQUENCE: 3

Cys Lys Ser Xaa Gly Ser Ser Cys Ser Xaa Thr Ser Tyr Asn Cys Cys
 1               5                  10                  15

Arg Ser Cys Asn Xaa Tyr Thr Lys Arg Cys Tyr
            20                  25

<210> SEQ ID NO 4
<211> LENGTH: 28
<212> TYPE: DNA
<213> ORGANISM: Artificial Sequence
<220> FEATURE:
<223> OTHER INFORMATION: primer

<400> SEQUENCE: 4
ttgtacagtg agatggaccc tgaggagc                                        28

<210> SEQ ID NO 5
<211> LENGTH: 30
<212> TYPE: DNA
<213> ORGANISM: Artificial Sequence
```

-continued

```
<220> FEATURE:
<223> OTHER INFORMATION: primer

<400> SEQUENCE: 5
ggcctccagg tcacagtgag gttccttggg                                   30

<210> SEQ ID NO 6
<211> LENGTH: 713
<212> TYPE: DNA
<213> ORGANISM: Mus musculus

<400> SEQUENCE: 6
ggcattgtac agcgagatgg accctgagga gcgcctgcgt tatgccagca cgcgccatgt    60
gaggccagac atgaagacac acatggaccg accectagtg gtggagcctg gtcgagatgg   120
cttgcgggga cccgttggga gcaagtcaaa gcctgaaggc acggaggcca cagaaagcgc   180
ggacctacct cgcaggcacc accggcaccg tgatagggac aagacctcag ccacagcacc   240
tgctggaggc gaacaggaca ggacagaaag caccgagacc ggggcccggg aggaacgtgc   300
gcgccctcgt cgaagtcaca gcaaggagac tccaggggct gacacgcaag ttgcgctgtg   360
agcgcagtaa acgtcaccac cggcgcggct ccccggagga ggccactgaa cgggagcttc   420
ggcgccaccg tgcccaccgg catgcacagg actcaagcaa ggagggcacg gcgccggtgc   480
ttgtacccaa gggtgagcga cgagcaagac accgaggccc acgcacgggt ccacgtgagg   540
cagagaacaa cgaggagccc acacgcaggc accgtgcaag gcataaggtg ccacccacac   600
tgcagccccc agagagggag gctgcagaga aggagagcaa cgcggtggaa ggggataagg   660
aaacccgaaa tcaccagccc aaggaacctc actgtgacct ggagaccaat gcc          713

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
aggcagcctt tgttttagca caaacaaagc                                   30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gcctgcttgc cgaatatcat ggtggaaaat                                   30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
ggtcgagatg gcttgcggga cccgttggga                                   30

<210> SEQ ID NO 10
<211> LENGTH: 30
<212> TYPE: DNA
```

```
<213> ORGANISM: Artificial Sequence
<220> FEATURE:
<223> OTHER INFORMATION: primer

<400> SEQUENCE: 10 tggcaccta  tgccttgcac  ggtgcctgcg                                          30
```

N-CALCIUM CHANNEL KNOCKOUT ANIMAL

This application is the U.S. National Phase under 35 U.S.C. §371 of International Application PCT/JP00/07503, filed Oct. 26, 2000, which claims priority to Japanese Patent Application No. 11-303809, filed Oct. 26, 1999, Japanese Patent Application No. 2000-37839, filed Feb. 16, 2000, and Japanese Patent Application No. 2000-261979, filed Aug. 31, 2000. The International Application was not published under PCT Article 21(2) in English.

TECHNICAL FIELD

The present invention relates to an animal deficient in N-type calcium channel and use thereof.

BACKGROUND ART

Calcium channels (Ca channels) are membrane proteins that transmit information into cells by controlling influx of $Ca^{2+}$ into the cells. In particular, voltage-dependent Ca channels present in excitatory cells such as nerve cells and muscle cells are proteins that play an important role of converting information transmitted through changes in membrane potential, into intracellular information which is an increase in $Ca^{2+}$ concentration.

Various voltage-dependent Ca channels have been identified from nerve cells and muscle cells (Bean, B. P. et al, Ann. Rev. Physiol., 51, pp. 367–384, 1989; Ross P., Ann. Rev. Neurosci., 56, p. 337, 1990), and these are classified into six types (L, N, P, Q, R and T) according to their electrophysiological properties and susceptibility to antagonists.

Among these Ca channels, N-type Ca channel is a Ca channel characterized in that $Ca^{2+}$ influx is inhibited by a peptide toxin isolated from cone shell, ω-conotoxin GVIA.

Calcium antagonists are widely used as antianginal drugs, antiarrhythmic drugs and therapeutic agents for hypertension, and their action mechanism is based on relaxation of vascular smooth muscles or suppression of myocardial contraction by inhibition of the $Ca^{2+}$ influx into a cell through a specific binding to the L-type Ca channel present in a cell membrane. Meanwhile, it is being revealed that $Ca^{2+}$ is an important factor for normal functions in nerves, such as release of nerve transmitter substances, formation of impulse patterns and outgrowth of neurites, while a $Ca^{2+}$ kinetics change is deeply involved in diseases such as delayed nerve cell death after cerebral ischemia and a certain kind of epilepsy (Siesjo, Mayo Clin Proc., 61, p. 299, 1986). Over the last few years, existence of P-, N-, Q- and R-type Ca channels, which are specifically present in nerves, were confirmed in addition to L-type and T-type. Roles of these Ca channels in nervous functions draw attentions, and novel calcium antagonists targeting them are being actively developed at the same time.

In particular, it has been reported that the N-type Ca channel is expressed at nerve endings of the autonomic nervous system, and its role in control through autonomic nerves is attracting attentions (Lane D. H. et al., Science, 239, pp. 57–61, 1988; Diane L, et al., Nature, 340, pp. 639–642, 1989).

Functions of the N-type Ca channel have hitherto been evaluated by conducting 1) an in vitro experiment using synaptosomes or cultured nerve cells or 2) an in vivo experiment using administration of ω-conotoxin GVIA. Since 1) is an in vitro experiment, it is not suitable for precise evaluation of the N-type Ca channel functions in living bodies. On the other hand, although 2) is an in vivo experiment, this is not suitable for precise evaluation of the N-type Ca channel functions in living bodies either because (1) selectivity of ω-conotoxin GVIA has not been completely elucidated, (2) ω-conotoxin GVIA is a peptide and hence it does not have sufficient permeability to a nerve cell, (3) a chronic-stage experiment using administration of ω-conotoxin GVIA is difficult and so forth.

DISCLOSURE OF THE INVENTION

In order to overcome the aforementioned drawbacks, preparation of an N-type Ca channel knockout mouse that is deficient only in the N-type Ca channel and can be used for a chronic-stage experiment has been strongly desired.

Accordingly, an object of the present invention is to prepare a knockout mouse which lacks $\alpha_{1B}$ subunit of the N-type Ca channel (referred to as "N-KO mouse" hereinafter). By using such a mouse, what functions the N-type Ca channel is actually responsible for in living bodies can be elucidated, which N-type Ca channel is considered to be expressed at nerve terminals of the central nervous system and the peripheral nervous system and plays an important role in maintenance of homeostasis of living bodies.

The N-KO mouse may not be able to maintain homeostasis through the autonomic nervous system, especially it cannot control blood pressure, and hence it may not survive normally. However, it was considered that, even though the N-KO mouse could not survive normally, the N-type Ca channel functions could be deduced from abnormalities observed in the N-KO mouse. Thus, it was attempted to prepare an N-KO mouse in which a gene coding for the $\alpha_{1B}$ subunit of the N-type Ca channel was disrupted by targeted disruption.

As a result, it was revealed that the N-KO mouse could undergo ontogenesis and growth and could produce offspring. Moreover, it was electrophysiologically proved that $Ca^{2+}$ influx that is inhibited by ω-conotoxin GVIA was not observed in nerve cells in dorsal root ganglia prepared from the N-KO mouse, and hence it was confirmed that the N-KO mouse lacked functional N-type Ca channel.

As a result of further studies, it was also revealed that the N-KO mouse had characteristics unique to deficiency in N-type Ca channel such as no blood-pressure reflex through nervous systems, insensitivity to pain and low blood sugar level compared with a wild-type mouse, and that the N-KO mouse was useful for analysis of N-type Ca channel functions in living bodies. Thus, the present invention has been accomplished.

That is, the present invention provides a non-human animal in which a gene coding for an N-type Ca channel is disrupted to lack functional N-type Ca channel (hereinafter, also referred to as "animal of the present invention"). The non-human animal is preferably a rodent, more preferably a mouse.

The gene coding for the N-type Ca channel is preferably a gene coding for an $\alpha_{1B}$ subunit of the N-type Ca channel. More specifically, there can be mentioned a gene comprising DNA defined in the following (a) or (b):

(a) DNA which comprises the nucleotide sequence of SEQ ID NO: 1;

(b) DNA which is hybridizable with DNA comprising the nucleotide sequence of SEQ ID NO: 1 under a stringent condition and codes for an $\alpha_{1B}$ subunit of functional N-type calcium channel.

The present invention also provides a method for determining an action of a substance, which comprises steps of administering a substance to the animal of the present invention and determining an action of the substance on the animal (hereafter, also referred to as "the determination method of the present invention").

The determination method of the present invention preferably comprises steps of administering a substance to the animal of the present invention and a wild-type animal, and comparing actions of the substance on the animal of the present invention and the wild-type animal to determine the action of the substance on the N-type calcium channel.

The present invention further provides a method for screening for a substance having a pharmacological action, which comprises a step of determining a pharmacological action of a substance by the determination method of the present invention, a substance having a pharmacological action obtained by this screening method and a method for manufacturing a drug, which comprises steps of screening for a substance having a pharmacological action by the screening method and manufacturing a drug comprising the obtained substance as an active ingredient.

As the pharmacological action, there can be mentioned an action for lowering blood pressure, an analgesic action and an action for lowering blood sugar level. Substances having such pharmacological actions can be used to manufacture hypotensive drugs, analgesic drugs and hypoglycemic drugs comprising these substances as active ingredients, respectively.

BEST MODE FOR CARRYING OUT THE INVENTION

Figure 1:
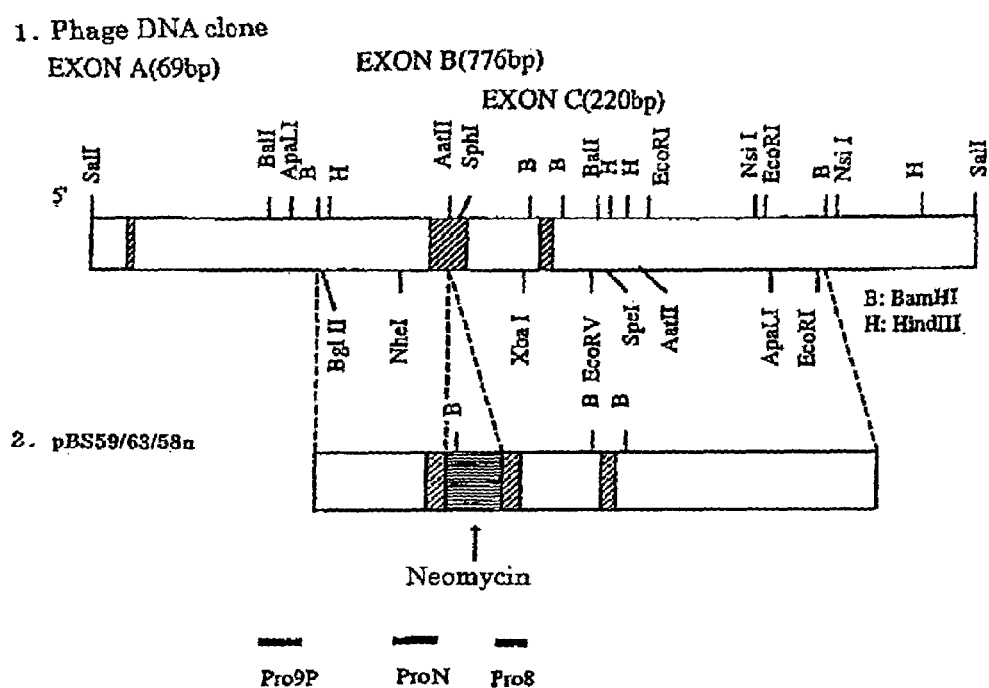
FIG. 1 shows a restriction enzyme map of a phage DNA clone and pBS59/63/58n.

Hereafter, embodiments of the present invention will be explained in detail.

As described above, the inventors of the present invention found that a mouse deficient in functional N-type Ca channel underwent ontogenesis and growth and could produce offspring, and that this mouse was useful for analysis of N-type Ca channel functions in living bodies. The animal of the present invention is based on these findings and is characterized by being a non-human animal wherein a gene coding for the N-type Ca channel is disrupted to lack functional N-type Ca channel.

Disruption of a gene means introducing a mutation into the gene so that function of its gene product is lost. As a method for disrupting a gene, there can be mentioned targeted disruption. The targeted disruption is a method for disrupting a gene by gene targeting, and refers to a mutation introducing technique wherein DNA having a nucleotide sequence of a target gene into which a mutation by which function of the gene product is lost is introduced, preferably DNA having a nucleotide sequence of a target gene into which a selective marker, more preferably a drug resistance gene is inserted, so that function of the gene product is lost, is introduced into a cell, and a cell having undergone homologous recombination between the introduced DNA and the target gene is selected (Suzanne L. et al., Nature, 336, p. 348, 1988). The targeted disruption mentioned herein is an example of a technique for disrupting the gene coding for an N-type Ca channel based on information about the nucleotide sequence of the gene, and any techniques fall within the scope of the present invention so long as a gene is disrupted based on information about the nucleotide sequence thereof.

Further, lack of a functional N-type Ca channel means that there is no longer substantial influx of $Ca^{2+}$ passed through the N-type Ca channel and can be verified by absence of substantial influx of $Ca^{2+}$ inhibited by ω-conotoxin GVIA. The ω-conotoxin GVIA referred to herein is a peptide purified from cone shell (*Conus geographus*) toxin (Baldomero, M. O. et al., Biochemistry, 23, p. 5087, 1984), and it is characterized by the amino acid sequence of SEQ ID NO: 3.

A gene coding for an N-type Ca channel means a gene coding for a constitutional subunit contained only in the N-type Ca channel, for example, the $α_{1B}$ subunit.

Specific examples of the gene coding for the $α_{1B}$ subunit include a gene having DNA defined in the following (a) or (b): (a) DNA which comprises the nucleotide sequence of SEQ ID NO: 1;

(b) DNA which is hybridizable with DNA comprising the nucleotide sequence of SEQ ID NO: 1 under a stringent condition and codes for the $α_{1B}$ subunit of a functional N-type calcium channel.

An example of the stringent condition mentioned herein include the conditions of hybridization at 65° C. in 4×SSC and subsequent washing at 65° C. in 0.1×SSC for 1 hour. The stringent condition may alternatively be 42° C., 4×SSC in 50% formamide.

The non-human animal is preferably a rodent, more preferably a mouse.

The animal of the present invention can be prepared according to a usual method for preparing a knockout animal by gene targeting except that the gene coding for an N-type Ca channel is used as a target gene.

Hereafter, cloning of the N-type Ca channel $α_{1B}$ subunit gene, construction of a targeting vector used in targeted disruption and acquisition of an embryonic stem cell (ES cell) having undergone homologous recombination will be explained in this order by exemplifying targeted disruption of a gene coding for an N-type Ca channel.

1. Cloning of DNA Including Part of N-type Ca Channel $\alpha_{1B}$ Subunit Gene DNA coding for the N-type Ca channel $\alpha_{1B}$ subunit can be obtained by designing primers based on the nucleotide sequence described in Thlerry, C. et al., FEES Letters, 338, p. 1, 1994 and performing PCR using non-human animal genomic DNA or cDNA or performing RT-PCR using non-human animal RNA. Alternatively, a probe may be synthesized based on the nucleotide sequence described in the aforementioned reference, and clones hybridizable with the probe may be selected from a non-human animal genomic DNA library or cDNA library and determined for the nucleotide sequences to select a clone containing the N-type Ca channel $\alpha_{1B}$ subunit gene or a part thereof comprising a nucleotide sequence of preferably 500 bp or more, more preferably 1 kbp or more.

A restriction enzyme map is prepared by determining restriction enzyme sites contained in the cloned DNA. In the case where a clone containing DNA of a length enough to cause homologous recombination, i.e., a clone of preferably 7 kbp or longer, more preferably 10 kbp or longer, is not obtained, DNAs may be excised from a plurality of clones at appropriate restriction enzyme sites and ligated.

2. Construction of Targeting Vector

A positive selection marker such as a drug resistance gene, preferably a neomycin resistance gene, is introduced into a restriction enzyme site of an exon region in the obtained DNA having a length enough to cause homologous recombination. Further, a part of the exon may be eliminated and replaced with a drug resistance gene. When there is no appropriate restriction enzyme site, appropriate restriction enzyme sites may be introduced by PCR using a primer designed so as to include restriction enzyme sites, ligation of oligonucleotides including restriction enzyme sites and so forth.

Preferably, the vector includes a negative selection marker such as thymidine kinase gene and diphtheria toxin gene in order to eliminate ES cells that do not undergo homologous recombination between the introduced DNA and the N-type Ca channel $\alpha_{1B}$ subunit gene in which the introduced DNA is inserted into a site that is not the N-type Ca channel $\alpha_{1B}$ subunit gene.

These recombinant DNA techniques for manipulating DNA nucleotide sequences can be implemented according to, for example, the methods described in Sambruck, J., Fritsch, E. F., and Maniatis, T., "Molecular Cloning: A Laboratory Manual", Cold Spring Harbor Laboratory, Cold Spring Harbor, N.Y., 1989, but such techniques are not limited to these methods so long as appropriate recombinant DNA can be obtained.

3. Acquisition of Embryonic Stem Cell (ES Cell) Having Undergone Homologous Recombination The prepared targeting vector is digested with restriction enzymes to form linear DNA, purified by, for example, phenol/chloroform extraction, agarose electrophoresis, ultracentrifugation and so forth and transfected into an ES cell, for example, TT2. Examples of the transfection method include electroporation, lipofection and so forth, but the present invention is not limited to these methods.

The transfected cell is cultured in an appropriate selection medium, for example, a selection medium containing neomycin and ganciclovir when a targeting vector incorporated with a neomycin resistance gene and a thymidine kinase gene is constructed.

It is readily confirmed by PCR or the like that an introduced gene, for example, a neomycin resistance gene, is incorporated into an ES cell that shows resistance to the both drugs and grows. Further, occurrence of the homologous recombination can also be confirmed by Southern blotting analysis using a 5' upstream or 3' downstream part of DNA outside the targeting vector as a probe. Further, it can be confirmed by Southern blotting analysis using DNA with the targeting vector as a probe that the targeting vector is not randomly inserted. An ES cell having undergone homologous recombination can be obtained by combining these methods.

An example of a method for preparing a knockout mouse will be described below, but the present invention is not limited to this example.

A knockout mouse is prepared by taking steps of collection of an 8-cell embryo or a blastocyst after fertilization, microinjection of an ES cell having undergone homologous recombination, implantation of a manipulated egg into a pseudopregnant mouse, delivery from the pseudopregnant mouse and raising of offspring, selection of a transgenic mouse by PCR and Southern blotting, and establishment of pedigree of mice having the introduced gene (Yagi, T. et al., Analytical Biochem., 214, p. 70, 1993).

1. Collection of 8-Cell Embryo or Blastocyst

As for fertilized eggs, 5 IU of pregnant mare's serum gonadotropin and 2.5 IU of human chorionic gonadotropin are intraperitoneally administered to a female mouse in order to induce superovulation, and an 8-cell embryo is obtained from the female mouse on day 2.5 after fertilization by the oviduct-uterus perfusion method. When a blastocyst is used, the uterus of a female mouse is removed on day 3.5 after fertilization and an embryo is obtained by uterus perfusion.

2. Microinjection of ES Cell Having Undergone Homologous Recombination

An ES cell having undergone homologous recombination is microinjected into the obtained 8-cell embryo or blastocyst. The microinjection can be performed under an inverted microscope by using a micromanipulator, microinjector, injection pipette and holding pipette based on, for example, the descriptions in Hogan, B. L. M., "A laboratory Manual", Cold Spring Harbor Laboratory Press, Cold Spring Harbor, N.Y., 1986 (Yagi, T. et al., Analytical Biochem., 214, p. 70, 1993). Further, as an injection dish, for example, there are used 5-μl medium droplets and droplets containing floating ES cells formed on Falcon 3002 (Becton Dickinson Labware), on which liquid paraffin is overlaid. Hereinafter, an 8-cell embryo or blastocyst microinjected with an ES cell having undergone homologous recombination is referred to as a manipulated egg.

3. Implantation of Manipulated Egg into Pseudopregnant Mouse

A vasoligated male mouse and a normal female mouse are mated to prepare a pseudopregnant mouse, into which a manipulated egg is implanted. Implantation of a manipulated egg can be performed based on, for example, the descriptions in Hogan, B. L. M., "A laboratory Manual", Cold Spring Harbor Laboratory Press, Cold Spring Harbor, N.Y., 1986 and Yagi, T. et al., Analytical Biochem., 214, P. 70, 1993. An example of specific procedure will be described below, but the present invention is not limited to this example.

A pseudopregnant mouse is generally anesthetized by using, for example, 50 mg/kg body weight of pentobarbital sodium. Then, both flanks are incised about 1 cm to expose the ovary and the oviduct. The bursa ovarica is incised by using tweezers under a stereoscopic microscope to expose the fimbriae tubae. Subsequently, 7 to 8 manipulated eggs per oviduct are introduced into the fimbriae tubae. At this time, implantation of the manipulated eggs into the oviduct is confirmed by micro air bubbles inserted together with the manipulated eggs. Then, the oviduct and the ovary are returned to the abdominal cavity, both of the incision sites are sutured, and the mouse is awakened from the anesthesia. In some cases, manipulated eggs may be cultured until the following day to be developed into a blastocyst and then implanted into the uterus.

4. Delivery from Pseudopregnant Mouse and Raising of Offspring

In many cases, offspring mice can be obtained on day 17 after the implantation. The offspring mice are usually chimeric mice obtained from the ES cell having undergone homologous recombination and a cell of the mouse from which the fertilized egg is collected. For example, when TT2 is used as an ES cell and injected into an 8-cell embryo collected from ICR, an offspring mouse having a high chimeric rate shows an agouti-dominant coat color, while a mouse having a low chimeric rate shows a white-dominant coat color.

5. Screening for Gene-Introduced Mouse by PCR and Southern Blotting

Whether the gene is present in a germ cell can be readily confirmed by the coat color of an offspring mouse obtained by mating a mouse of interest with a mouse having a white coat color, for example, ICR. Alternatively, since a mouse having a high chimeric rate is expected to also have a germ cell containing the introduced gene, the presence or absence of the gene can be confirmed by using a mouse having a chimeric rate as high as possible for mating, extracting DNA from the tail of the obtained offspring mouse and subjecting its DNA to PCR. Further, a genotype can be more reliably identified by performing Southern blotting analysis instead of PCR.

6. Establishment of Lineage of Mice Having Introduced Gene

An N-KO mouse in which the introduced gene homozygously exists can be obtained among the offspring mice obtained by mating heterozygous mice (hereinafter, referred to as He mice) with each other. The N-KO mouse can be obtained by mating He mice with each other, a He mouse with an N-KO mouse, or N-KO mice with each other.

The presence or absence of expression of the $\alpha_{1B}$ subunit mRNA in the N-KO mouse can be confirmed by Northern blotting analysis, RT-PCR, RNase protection assay, in situ hybridization or the like. Further, expression of the $\alpha_{1B}$ subunit protein can be confirmed by immunohistochemical staining, labeled ω-conotoxin or the like. Further, a function of an N-type Ca channel including the $\alpha_{1B}$ subunit can also be confirmed by an electrophysiological method or the like.

Moreover, as described above, the inventors of the present invention found that an animal lacking the gene coding for an N-type Ca channel lost blood pressure control through the autonomic nervous system, had defects in a mechanism for transmitting pain, especially second phase pain that appears in a delayed manner, and had abnormality in blood sugar level control. That is, they found that the animal had unique characteristics associated with the deletion of the gene coding for an N-type Ca channel. The determination method of the present invention is based on these findings and it is a method for determining an action of a substance that comprises steps of administering a substance such as a compound to the animal of the present invention and determining the action of the substance on the animal.

The determination method of the present invention preferably comprises steps of administering a substance to the animal of the present invention and a wild-type animal and comparing actions of the substance on the animal of the present invention and the wild-type animal to determine the action of the substance on the N-type Ca channel. The influence of the substance on the N-type Ca channel can be examined by determining the action on the N-type Ca channel.

An action refers to an action on a characteristic unique to the animal. For example, when attention is paid to abnormality of the animal in blood pressure control, transmission of pain or blood sugar level control, the action refers to an action on the blood pressure, pain or blood sugar level. However, the action is not limited to these examples so long as the action is associated with the characteristics unique to the animal. These actions can be determined as activities of the substances.

Further, a wild type means that functional N-type Ca channel is not lost.

The present invention further provides a method for screening for a substance having a pharmacological action by using the animal of the present invention (non-human animal deficient in N-type Ca channel). Specifically, a method for screening for a substance having a pharmacological action, for example, a substance acting on blood pressure, transmission of pain or blood sugar level of the animal (that is, a substance having an action for lowering blood pressure, a substance having an analgesic action or a substance having an action for lowering blood sugar level) by using the determination method of the present invention, a substance obtained by the screening and a method for manufacturing a drug that comprises steps of screening for a substance having a pharmacological action by using the determination method of the present invention and manufacturing a drug (for example, hypotensive drug, analgesic drug or hypoglycemic drug) containing the obtained substance as an active ingredient.

As examples, a substance having an action for lowering blood pressure, a substance having an analgesic action or a substance having an action for lowering blood sugar level will be described below in this order. However, any substances fall within the scope of the present invention so long as they are obtained by utilizing a screening system using the animal of the present invention.

1. Method for Screening for Substance Having Action for Lowering Blood Pressure (Hypotensive Drug)

Candidate substances can be screened for a substance having an action for lowering blood pressure through blocking the influx of $Ca^{2+}$ passed through N-type Ca channel by administering each of the candidate substances to a non-human animal deficient in the N-type Ca channel (N-KO animal) and a wild-type animal not deficient in the channel (Wt animal) and selecting a drug that lowers blood pressure in the Wt animal, but not in the N-KO animal.

Further, on the contrary, candidate substances can be screened for a substance having an action for lowering blood pressure without blocking the influx of $Ca^{2+}$ passed through the N-type Ca channel by selecting a substance having an action for lowering blood pressure in the N-KO animal. Although the N-KO mouse of the present invention had been expected to be deficient in blood pressure control through nervous systems, the average blood pressure of the N-KO mice was higher than that of the wt animals and this suggested that a blood pressure control system through an endogenous factor intensely operated in the N-KO animal. Therefore, the N—RO animal is particularly useful for screening for a substance having an action for lowering blood pressure through an endogenous factor.

Specifically, for example, when an N-KO mouse and a wild-type mouse (hereinafter, referred to as Wt mouse) are used, following anesthetization of each mouse, a tube is placed in the trachea and artificial respiration is attained by using an animal ventilator with air ventilation of 0.2 ml at a respiratory frequency of 140 breaths/min. A polyethylene tube filled with a physiological saline containing heparin is inserted into the right common carotid artery and connected to a pressure transducer to measure the blood pressure. Each of candidate substances to be subjected to the screening is administered by using an indwelling catheter placed in the left common carotid artery, and a substance having an action for lowering the blood pressure is selected from the candidates.

2. Method for Screening for Substance Having Analgesic Action (Analgesic Drug)

Candidate substances can be screened for a substance having an analgesic action through or not through blocking of the influx of $Ca^{2+}$ passed through N-type Ca channel by administering the candidate substances to an N-KO animal and a Wt animal and comparing their analgesic actions. The analgesic action can be confirmed by, for example, a formalin test, hot-plate test, acetic acid-induced writhing test, tail-flick test, tail-pinch test or the like.

Specifically, for example, in the case of a formalin test using an N-KO mouse and a Wt mouse, 20 μl of 3% formalin is subcutaneously administered to each of the N-KO mouse and the Wt mouse at the sole of the left hind leg. Then, the duration of the mouse's behavior of licking its left hind leg (licking) was measured over 30 minutes for use as an indicator of pain. Substances subjected to the screening are administered, and a substance reducing the pain indicator can be selected.

3. Method for Screening for Substance Having Action for Lowering Blood Sugar Level (Hypoglycemic Drug)

Candidate substances can be screened for a substance having a hypoglycemic action through or not through blocking of the influx of $Ca^{2+}$ passed through N-type Ca channel by administering each of the candidate substances to an N-KO animal and a wt animal and comparing their hypoglycemic actions.

Specifically, for example, when an N-KO mouse and a Wt mouse are used, blood is collected from the caudal vein of each of the N-KO mouse and the Wt mouse under a fed condition (fasted for 2 hours prior to blood collection) or a fasted condition (fasted for 18 hours) and the blood sugar level is measured. The blood sugar level can be measured, for example, as follows. 10 μl of blood and 90 μl of 0.6 N perchloric acid are mixed and subjected to centrifugation (7,000 rpm, 2 min). Then, 20 μl of the supernatant and 300 μl of color developing solution of Glucose CII-Test Wako (Wako Pure Chemical Industries) are mixed and allowed to react at 37° C. for 5 minutes, and absorption of the reaction mixture is measured at 505 nm.

A drug containing a substance having a pharmacological action as an active ingredient can be manufactured according to a usual drug preparation method. The drug may be a pharmaceutical composition of a substance having a pharmacological action and a pharmaceutically acceptable carrier.

EXAMPLES

The present invention will be explained more specifically with reference to the following examples. However, the scope of the present invention is not limited to these examples.

Example 1

Disruption of Gene Coding for N-type Ca Channel by Gene Targeting (1) Cloning of Gene Coding for N-type Ca Channel $\alpha_{1B}$ Subunit Primers (SEQ ID NOS: 4 and 5) were designed based on the nucleotide sequence of the mouse $\alpha_{1B}$ subunit gene described in FEBS Letters, 338, pp. 1–5, 1994, and PCR was performed by using the mouse cDNA library as a template to obtain DNA having the nucleotide sequence of SEQ ID NO: 6. By using this DNA as a probe, a phage DNA clone with a part of the gene coding for the N-type Ca channel $\alpha_{1B}$ subunit was isolated from a 129SVJ-derived mouse genomic library (λFIXII). The restriction enzyme map of the obtained phage DNA clone is shown in FIG. 1.

(2) Construction of Targeting Vector

A targeting vector was prepared by a method wherein a region including exon B in the $\alpha_{1B}$ subunit gene was used as a homologous gene region; a neomycin resistance gene was introduced into the exon B (FIG. 1), and the thymidine kinase gene of herpes simplex virus was introduced as a negative selection gene (Suzanne, L. et al., Nature, 336, p. 348, 1988).

Figure 2:
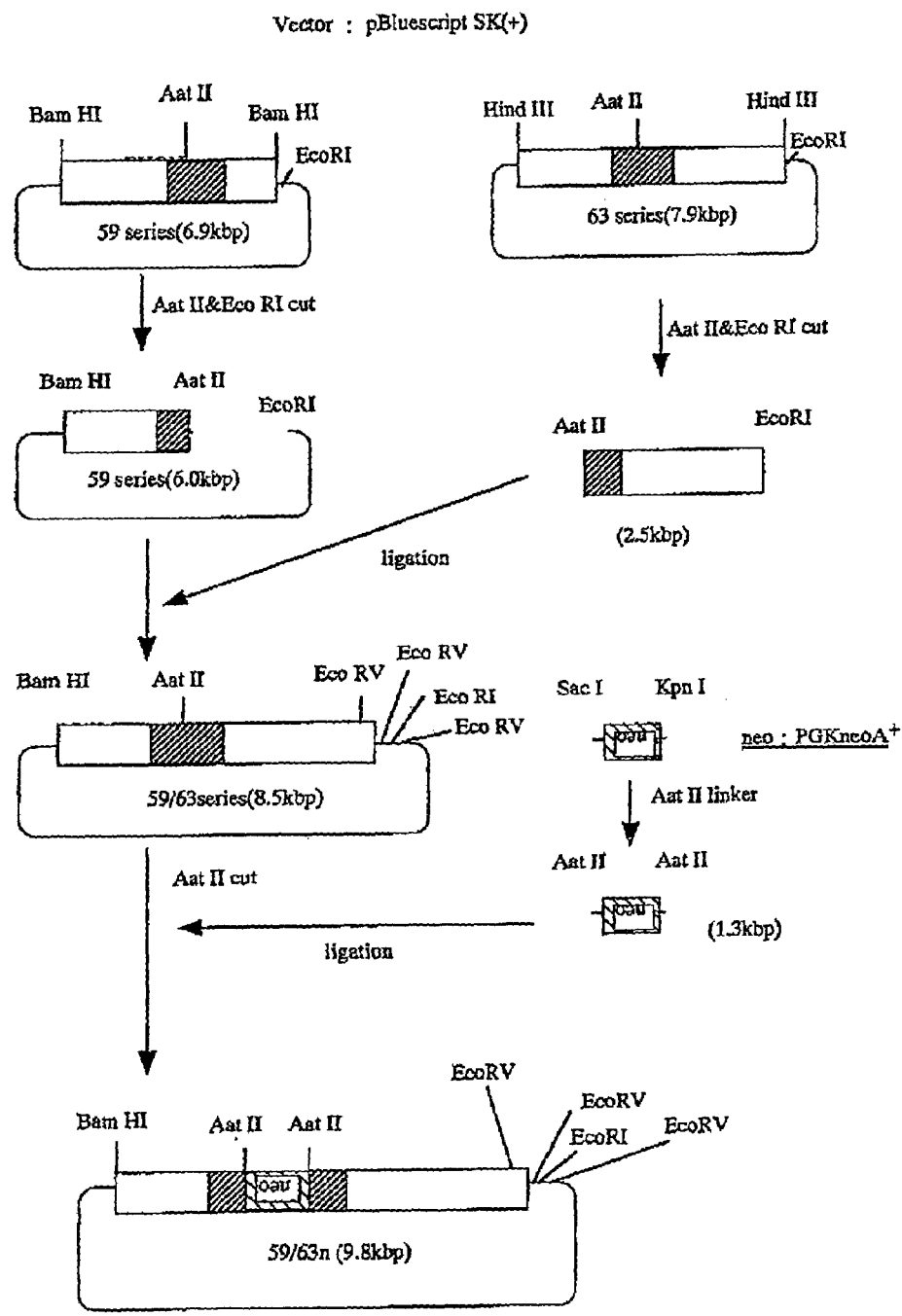
FIG. 2 shows preparation of a targeting vector.
Figure 3:
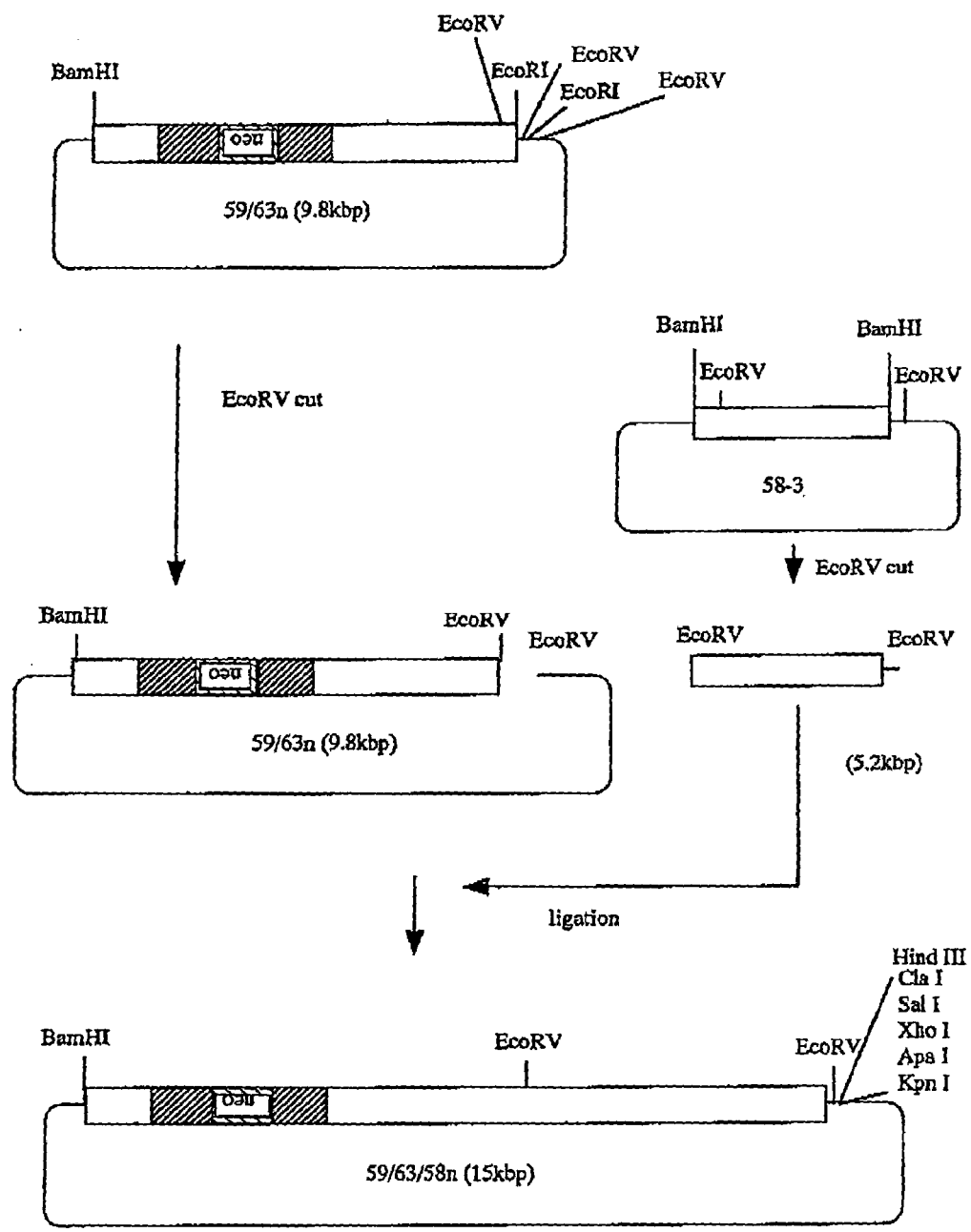
FIG. 3 shows preparation of a targeting vector.
Figure 4:
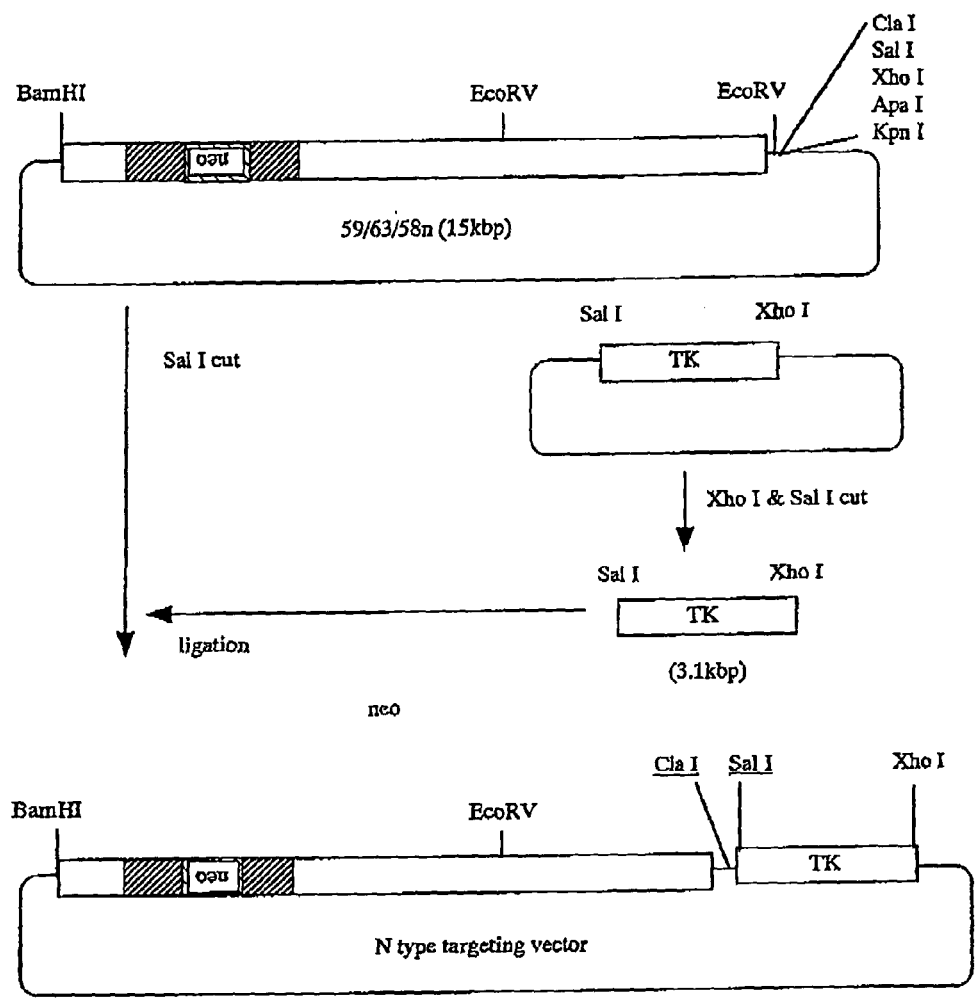
FIG. 4 shows preparation of a targeting vector.

Outline of the construction is shown in FIGS. 2–4. The phage DNA clone obtained in (1) was digested with BamHI and subcloned into pBluescript II SK+ to obtain pBS59 and pBS58 having the fragments shown in FIGS. 2 and 3. The phage DNA clone was also digested with HindIII and subcloned into pBluescript II SK+ to obtain pBS63 having a fragment shown in FIG. 2. The pBS59 was digested with AatII and EcoRI and a fragment excised from pBS63 with AatII and HindIII was introduced thereto to obtain pBS59/63. This pBS59/63 was digested with AatII and a fragment including the neomycin resistance gene was introduced thereto to prepare pBS59/63n. This was further digested with EcoRV and a fragment excised from pBS58 with EcoRV wa introduced thereto to prepare pBS59/63/58n. The thymidine kinase gene, which is a selection gene, was introduced into the SalI-XhoI site of a multicloning site in pBS59/63/58n to produce a targeting vector.

(3) Acquisition of Embryonic Stem Cell (ES Cell) Having Undergone Homologous Recombination The targeting vector obtained in (2) was digested with NotI to form linear DNA (1 mg/ml). As a mouse ES cell, TT2 was used (Yagi, T. et al., Analytical Biochem. 214, p. 70, 1993). The linear targeting vector (200 μg/ml) was transfected into the ES cells (1×10⁷ cells/ml) by electroporation (250 V, 975 μF, room temperature), and the cells were cultured in a medium containing G418 (250 μg/ml) and ganciclovir (0.2 μM) for 3 days from day 2 of culture, and then cultured in a medium containing G418 (250 μg/ml) for 3 days. DNA was extracted from a part of the generated ES cell colonies, and PCR was performed by using this DNA as a template, and DNA having the nucleotide sequence (SEQ ID NO: 7) outside the targeting vector and DNA having the nucleotide sequence (SEQ ID NO: 8) included in the introduced gene (neomycin resistance gene) as primers. Clones generating 3.7-kb PCR product were assumed as candidates that have possibility of having undergone homologous recombination.

Among the candidate clones, a clone having undergone only homologous recombination was identified by Southern blotting analysis. The extracted genome was digested with ApaLI and BalI, hybridized with a probe Pro9P outside the targeting vector (about 0.9-kbp DNA 5'-upstream from the homologously recombined region was obtained by PCR, see FIG. 1) and a probe Pro8 inside the targeting vector (about 0.8-kbp DNA excised from pBS59 with SphI and BamHI, see FIG. 1). A clone having undergone homologous recombination was selected, that is, a clone was selected for which a 6.9-kb band was detected in the ApaL1 digestion product and a 4.6-kb band was detected in the BalI digestion product when Pro9P was used as a probe, while a 6.9-kb band was detected in the ApaL1 digestion product and a 2.4-kb band was detected in the BalI digestion product when Pro8 was used as a probe.

(4) Preparation of N-KO Mouse

To a female mouse, 5 IU of pregnant mare's serum gonadotropin (PMSG, Serotropin, Teikoku Hormone Mfg., Tokyo) and 2.5 IU of human chorionic gonadotropin (hCG, Gonatropin, Teikoku Hormone Mfg., Tokyo) were intraperitoneally administered. On day 2.5 after fertilization, an 8-cell embryo was obtained by the oviduct-uterus perfusion method.

To the 8-cell embryo, the ES cells having undergone homologous recombination obtained in (3) were microinjected under an inverted microscope (DIAPHOTO TMD, Nippon Kogaku Kogyo, Tokyo) by using a micromanipulator (coarse-adjustment electric manipulator equipped with a suspended type joystick three-dimensional oil hydraulic micromanipulator, Narishige, Tokyo), a microinjector (Narishige, Tokyo), an injection pipette and a holding pipette. Further, as an injection dish., there were used several 5-µl medium droplets containing floating ES cells formed on Falcon 3002 (Becton Dickinson Labware) and overlaid with liquid paraffin.

Vasoligated male mice and normal female mice were mated to prepare pseudopregnant mice, and manipulated eggs into which three different ES cell clones having undergone homologous recombination were microinjected were implanted in the pseudopregnant mice. The pseudopregnant mice were generally anesthetized with 50 mg/kg body weight of pentobarbital sodium (Nembutal, Abbott Laboratories). Then, both flanks were incised about 1 cm to expose the ovary and the oviduct. The bursa ovarica was incised by using tweezers under a stereoscopic microscope to expose the fimbriae tubae. Subsequently, 7 to 8 manipulated eggs per oviduct were transferred into the fimbriae tubae. Then, the oviduct and the ovary were returned to the abdominal cavity, and both the incision sites were sutured.

The mice in which the manipulated eggs were implanted to be pregnant delivered a 100% chimeric mouse with a black coat color. To confirm that germ cells of the obtained 100% chimeric mouse were derived from the ES cells, the chimeric mouse was mated with an ICR female mouse, and their offspring mice were examined. The coat color of all the offspring mice was black, and hence it was confirmed that the germ cells of the chimeric mouse were derived from the ES cells. He mice were obtained by mating the chimeric mouse with C57BL/6, and an N-KO mouse was obtained by mating He mice with each other.

The genotypes of the obtained mice were confirmed based on differences in size of DNA fragments generated by PCR. The tail of each mouse was excised in a length of about 2–3 mm and digested (55° C., 2 hours) with a proteinase K solution (lysis buffer (Perkin Elmer) was diluted two-fold with PBS(−), 1% mercaptoethanol, 0.25 mg/ml of proteinase K). Thereafter, genomic DNA was extracted by a usual method and dissolved in 100–200 µl of distilled water to prepare a template for PCR. Primers were designed for the sequence included in the neomycin resistance gene (SEQ ID NO: 8) and two sites in the $\alpha_{1B}$ subunit gene (SEQ ID NOS: 9 and 10), and PCR was performed to identify the genotype of each individual. The gene having undergone a mutation produced a 520-bp PCR product, whereas the wild-type gene produced a 490-bp PCR product.

As required, the genotype was also confirmed by Southern blotting analysis. When the genomic DNA extracted from the mouse tail was digested with BamHI, and a region adjacent to the neomycin resistance gene in the targeting vector was hybridized with a probe ProN (about 1-kbp DNA excised from pBS59 with NcoI, see FIG. 1), only a 3.1-kb band was detected for the N-KO mouse.

The expression amount of mRNA in mouse brain was confirmed by Northern blotting. Total RNA was extracted from each of brains of 3 mice having each genotype by the AGPC method. Purified mRNA was obtained from the total RNA by using an oligo dT column (Amersham Pharmacia Biotech). The mRNA (5 µg/lane) was subjected to electrophoresis on 0.5% gel and hybridized with DNA having the nucleotide sequence of SEQ ID NO: 6 as a probe. The Northern blotting analysis showed that the mRNA expressed in the Wt mouse had completely disappeared in the N-KO mouse.

(5) Confirmation of N-KO Based on Electric Current Passed Through N-type Ca Channel By using nerve cells in the dorsal root ganglia of the Wt mouse and the N-KO mouse, changes in the amount of $Ca^{2+}$ influx inhibited by the ω-conotoxin GVIA were measured by using $Ba^{2+}$ as a charge carrier by the whole-cell patch clamp method.

A 5- to 8-week old mouse was anesthetized with ether, and its dorsal root ganglia were removed and digested in a Krebs solution by using pronase (0.2 mg/ml) first for 30 minutes and then thermolysin (0.2 mg/ml) for 30 minutes to isolate cells.

A patch clamp amplifier (Axopatch 200B) was set at a whole cell mode, and measurement was performed at room temperature. A patch pipette (outer diameter: 1.5 mm, inner diameter: 1.1 mm) was prepared by using a P-87 Flaming-Brown micropipette puller (Sutter Instrument). A solution containing 3 mM $BaCl_2$, 155 mM tetraethylammonium chloride, 10 mM HEPES and 10 mM glucose (pH 7.4) was used as the outer solution of the isolated nerve cells and the patch pipette was filled with a solution containing 85 mM cesium aspartate, 40 mM CsCl, 2 mM $MgCl_2$, 5 mM EGTA, 2 mM ATPMg, 5 mM HEPES and 10 mM creatine phosphate (pH 7.4). The electric resistance of the pipette was 1–2 Mohm, and the current of $Ba^{2+}$ obtained by a stimulus at 100 kHz was analyzed by using pCLAMP (Axon Instruments). The currents of the total Ca channels of nerve cells were measured for the Wt mouse and the N-KO, and the ω-conotoxin GVIA (1 µM) was added to measure the current other than that for N-type Ca channel.

Figure 5:
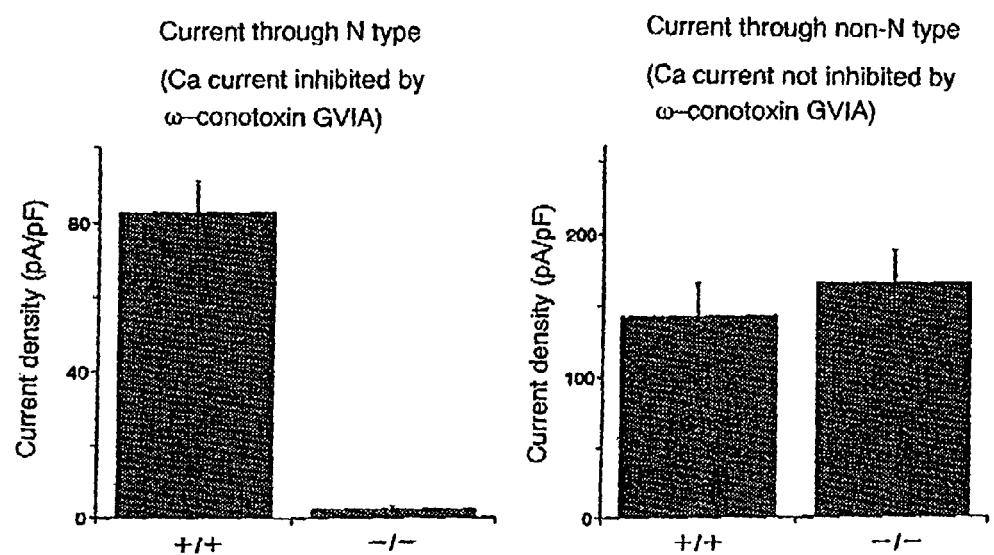
FIG. 5 shows comparison of electric currents passed through N-type Ca channels of an N-KO mouse and a wild-type mouse.

The results are shown in FIG. 5. The values in the figure are average values, and the bars represent standard deviations (Wt (+/+): n=4, N-KO (−/−): n=7). It was electrophysiologically proved that the influx of $Ca^{2+}$ inhibited by the ω-conotoxin GVIA was not observed in nerve cells of the nerve dorsal root ganglia extracted from the N-KO mouser and thus it was confirmed that the N-KO mouse lacked functional N-type Ca channel.

(6) Comparison of Body Weight, Heart Rate and Blood Pressure Between Genotypes

Body weight, heart rate and average blood pressure of a Wt mouse and those of an N-KO mouse were compared and examined. The Wt mice (15- to 16-week old, male, n=4) and the N-KO mice (15- to 16-week old, male, n=4) were anesthetized with 10% urethane. Following tracheal intubation, artificial respiration was performed by using an animal ventilator (Columbs) with a ventilation volume of 0.2 ml at a respiratory frequency of 140 breaths/min. A polyethylene tube filled with physiological saline containing heparin was inserted into the right common carotid artery and connected to a pressure transducer (Millar, Model MPC-500) to measure the blood pressure. The heart rate was obtained from blood pressure pulsation.

Figure 6:
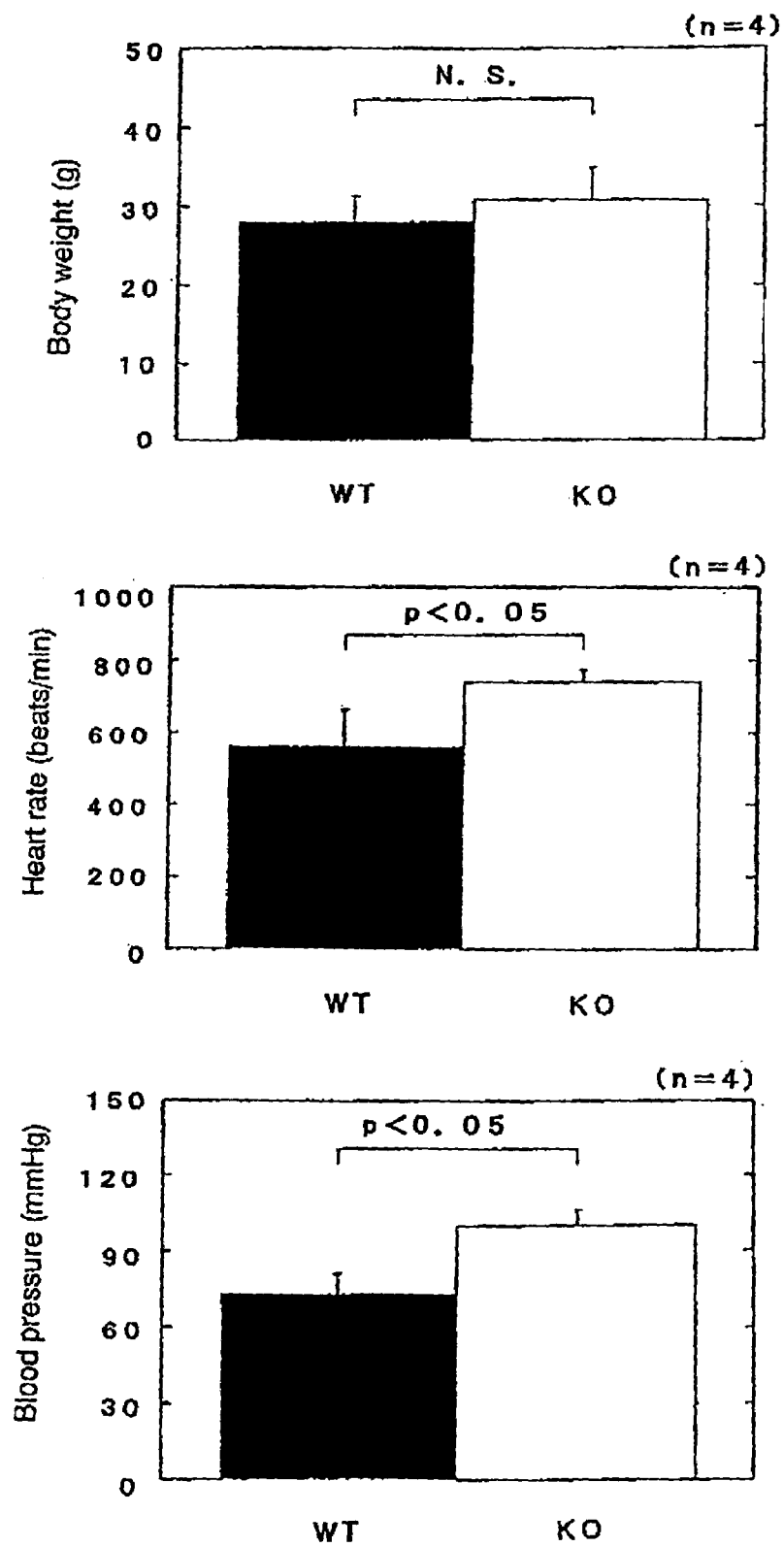
FIG. 6 shows comparison of heart rate and blood pressure of an N-KO mouse and those of a wild-type mouse.

The results are shown in FIG. 6. The values in the figure are average values, and the significant differences were determined by the t-test. There was no difference in body weight between the two groups (28.2±3.2 g vs. 30.8±4.0 g). The heart rate and the average blood pressure of the N-KO mice were significantly higher than those of the Wt mice (562±101.9 beats/min vs. 742±32.5 beats/min, $p<0.05$, 73.4±7.7 mmHg vs. 100.0±6.6 mmHg, $p<0.05$).

These results are considered to suggest a possibility that the heart rate and the blood pressure were maintained at a constant level due to vagotonia in the Wt mouse, whereas a vagotonia state was lost due to the lack of sympathetic innervation and parasympathetic innervation, and the heart rate and the blood pressure were significantly higher in the N-KO mouse. Further, it is also considered to be possible that the N-KO mouse constantly has higher levels of factors involved in the pressure rise such as nerve transmitter substances including noradrenaline, angiotensin II, endothelin etc.

Example 2

Changes in Blood Pressure Upon Administration of ω-Conotoxin GVIA to Mouse

Changes in heart rate and blood pressure of a Wt mouse and those of an N-KO mouse due to the ω-conotoxin GVIA were evaluated. Wt mice (15- to 16-week old, male, body weight 28.2±3.2 g, n=4) and N-KO mice (15- to 16-week old, male, body weight 30.8±4.0 g, n=4) were anesthetized with 10% urethane. Following tracheal intubation, artificial respiration was performed by using an animal ventilator (Columbs) with a ventilation volume of 0.2 ml at a respiratory frequency of 140 breaths/min. A polyethylene tube filled with physiological saline containing heparin was inserted into the right common carotid artery and connected to a pressure transducer (Millar, Model MPC-500) to measure the blood pressure. Further, a catheter was indwelled in the left common carotid artery to administer ω-conotoxin GVIA (omega-CgTx GVIA, 30 µg/kg).

Figure 7:
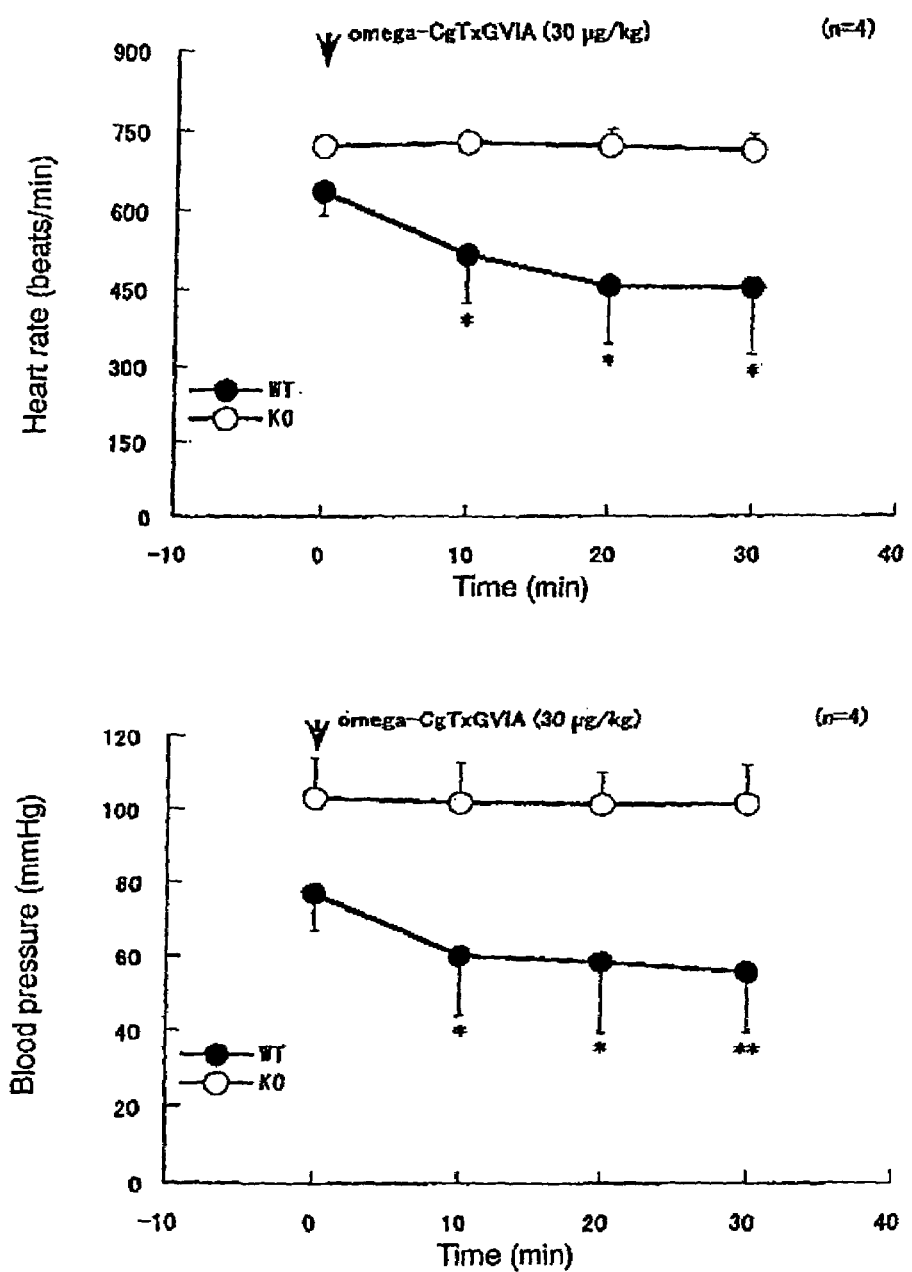
FIG. 7 shows comparison of changes in blood pressure of an N-KO mouse and a wild-type mouse, to ω-conotoxin was administered.

The results are shown in FIG. 7. The values in the figure are average values, and the bars represent standard deviations. In the wt mice., significant decreases in the heart rate and the blood pressure were observed from 10 minutes after the administration. On the other hand, no changes in the heart rate and the blood pressure were observed in the N-KO mouse even after the administration of ω-conotoxin GVIA.

These results suggest that N-type Ca channel should be involved in the controls of heart rate and blood pressure. Therefore, it is considered that the N-KO mouse is an animal model useful for elucidating the control mechanisms of heart rate and blood pressure.

Example 3

Experiment about Blood Pressure Control Mechanism—Examination of Blood Pressure Change with Bilateral Carotid Occlusion Blood pressure changes with bilateral carotid occlusion (henceforth referred to as BCO) in a Wt mouse and an N-KO mouse were evaluated. Wt mice (15- to 16-week old, male, body weight 28.2±3.2 g, n=4) and N-KO mice (15- to 16-week old, male, body weight 30.8±4.0 g, n=4) were anesthetized with 10% urethane. Following tracheal intubation, artificial respiration was performed by using an animal ventilator (Columbs) with a ventilation volume of 0.2 ml at a respiratory frequency of 140 breaths/minute. A polyethylene tube filled with physiological saline containing heparin was inserted into the right common carotid artery and connected to a pressure transducer (Millar, Model MPC-500) to measure the blood pressure. Further, a silk thread (Natsume, suture needle with thread, Black broad silk No. 8-0) for artery occlusion was placed on the left common carotid artery, and the blood flow was transiently stopped by holding the silk thread upward to obtain a BCO state.

Figure 8:
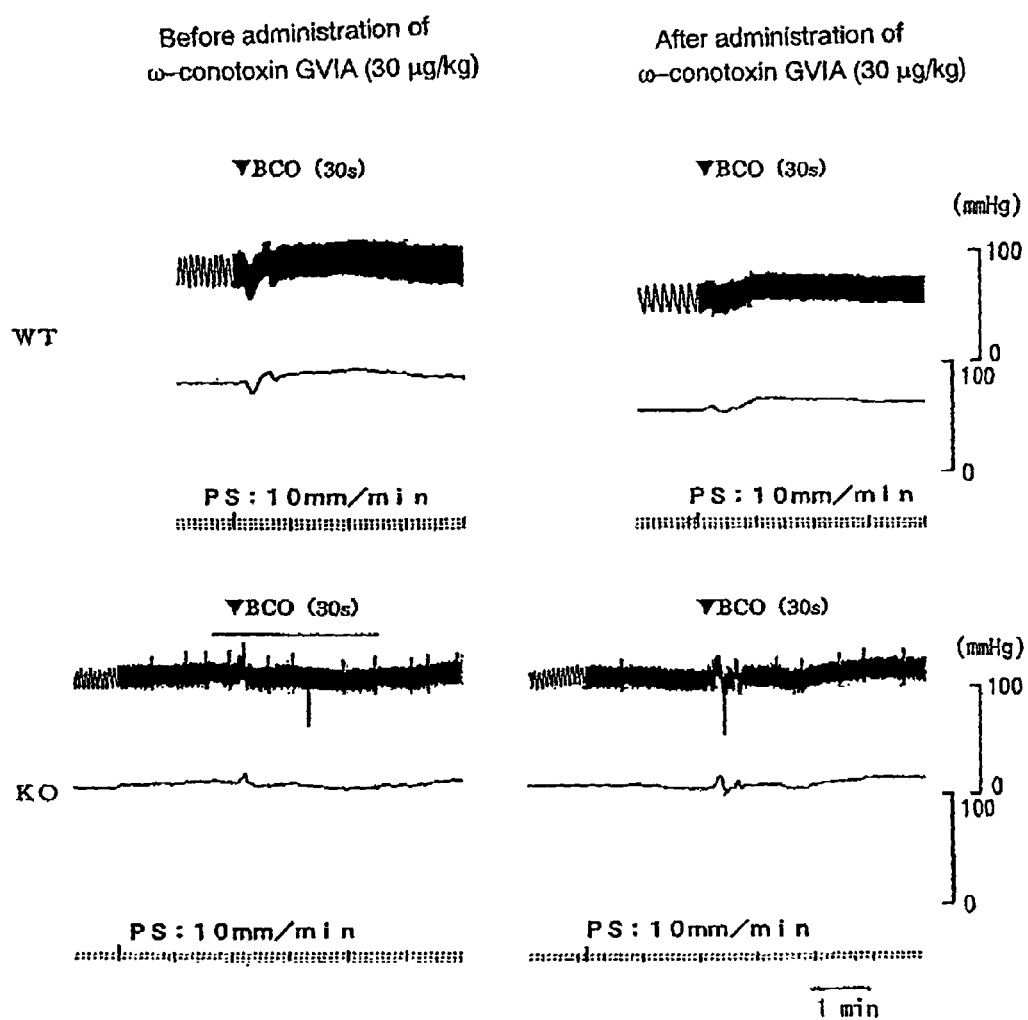
FIG. 8 shows comparison of changes in blood pressure of an N-KO mouse and a wild-type mouse, which were subjected to bilateral carotid occlusion (BCO).

As a result of BCO for 30 seconds, a transient rise of blood pressure was observed in the Wt mice, but this blood pressure rise mostly disappeared after the administration of ω-conotoxin GVIA (30 µg/kg). On the other hand, no blood pressure rise was observed in the N-KO mice even in the BCO state. Typical data are shown in FIG. 8 (upper lines: arterial pressure, lower lines: average blood pressure in FIG. 8).

From these results, it is considered that the N-KO mouse lacked a pressure reflex mechanism through a pressure receptor present in the internal carotid artery, and that nerve transmitter substances were not released at least from a neuroterminal of the sympathetic nerve postganglionic fiber.

It is considered that roles of Ca channel of each subtype at an autonomic neuroterminal involved in the cardiocirculatory control mechanism can be revealed by using the N-KO mouse.

Example 4

Examination of Analgesic Effect on Formalin Administration

In this experiment, a Wt mouse, He mouse and N-KO mouse (male, 6-week old) were used. 30 µl of formaldehyde solution (WAKO, 35.0–38.0%, first grade, Lot No. DLL4284) was added to 970 µl of physiological saline. This is referred to as 3% formalin. 20 µl of the 3% formalin was subcutaneously administered to the mouse at the sole of left hind leg. After the formalin was administered, the duration of the mouse's behavior of licking its left hind leg (licking) was measured over 30 minutes for use as an indicator of pain. The duration was summed up every 5 minutes and represented in seconds. The significant difference was obtained by performing a parametric one-way layout variance analysis and then Dunnet's multiple comparison test (*: $p<0.05$, **: $p<0.01$ vs. control group). In the test, a statistical analysis support system into which SAS 6.12 (SAS Institute Japan, Tokyo) was incorporated was used.

Figure 9:
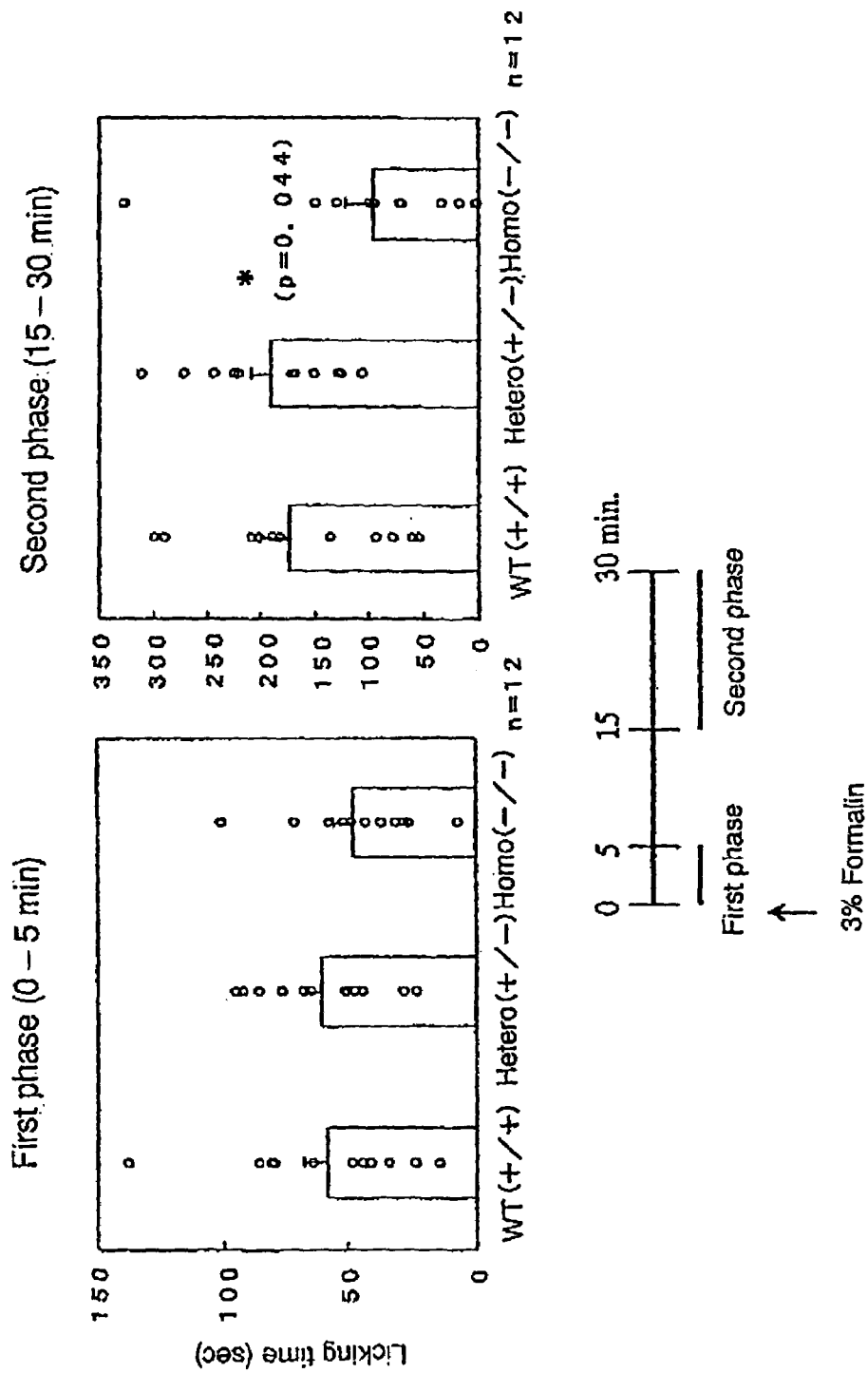
FIG. 9 shows comparison of susceptibilities of an N-KO mouse and a wild-type mouse to pain in a formalin test.

As a result, no difference was observed for pain in a first phase (0–5 minutes) in the N-KO mouse compared with the Wt mouse and the He mouse, but an analgesic effect was observed on pain in a second phase (15–30 minutes) (FIG. 9). This suggests that N-type Ca channel is involved in transmission of pain. It is also suggested that, since the transmission of pain is not completely suppressed, the N-KO mouse is useful for evaluation of analgesic drugs through action points other than N-type Ca channel.

Example 5

Blood Sugar Level of N-KO Mouse

1. Measurement of Blood Sugar Level of N-KO Mouse

10 µl of blood was collected from each caudal vein of N-KO mice and Wt mice (wt (+/+) male: n=9, Wt female: n=10, N-KO (−/−) male: n=10, N-KO female: n=10) under a fed condition (fasted for 2 hours prior to blood collection) or a fasted condition (fasted for 18 hours), mixed with 90 µl of 0.6 N perchloric acid and centrifuged (7,000 rpm, 2 min). 20 µl of the supernatant and 300 µl of a color developing solution of Glucose CII-Test Wako (wako Pure Chemical industries) were mixed on a 96-well microplate, and allowed to react at 37° C. for 5 minutes, and absorbance of the mixture was measured at 505 nm.

Figure 10:
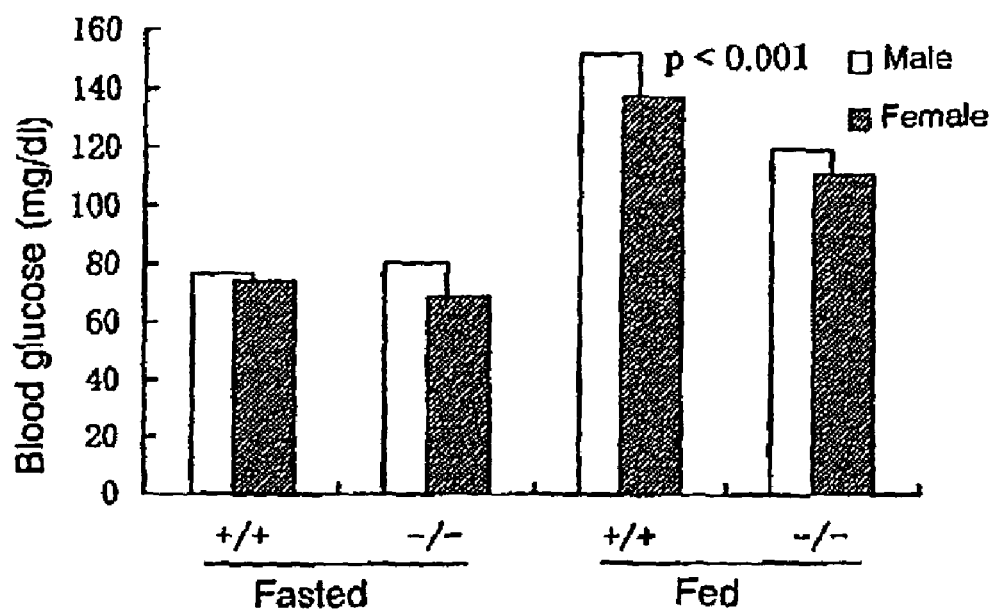
FIG. 10 shows comparison of blood sugar levels of an N-KO mouse and a wild-type mouse.

The results are shown in FIG. 10. The values in the figure are average values. In the case of the fed condition, the N-KO mice showed significantly low blood sugar levels compared with those of the Wt mice (t-test). On the other hand, under the fasted condition, no significant difference was observed between blood sugar levels of those mice.

These results show that blood sugar level can be raised by activation of nerve transmission through the N-type Ca channel and indicate that the N-type Ca channel should be involved in normalization of blood sugar level (maintenance of homeostasis).

2. Glucose Tolerance Test of N-KO Mouse

Figure 11:
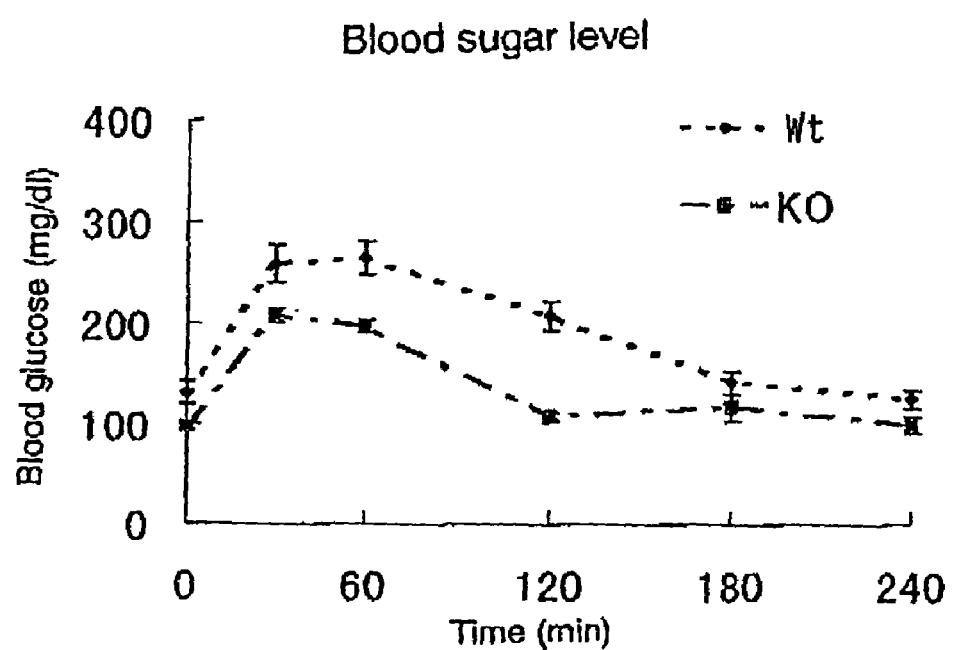
FIG. 11 shows comparison of blood sugar levels of an N-KO mouse and a wild-type mouse after glucose administration.
Figure 12:
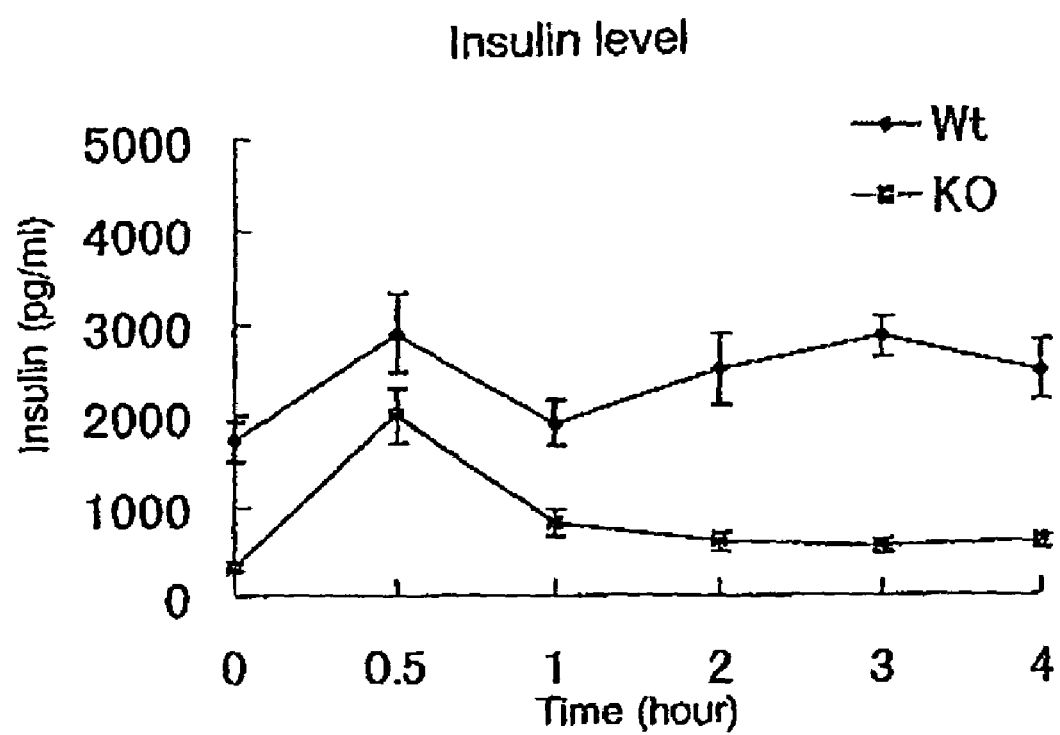
FIG. 12 shows comparison of blood insulin level of an N-KO mouse and a wild-type mouse after glucose administration.

Wt mice and N-KO mice (male, 9- to 10-month old, Wt: n=9, N-KO: n=9 for determination of blood sugar level, Wt: n=8, N-KO: n=9 for determination of insulin level) that had fasted for 16 hours were orally administered with 2 g/kg body weight of 20% glucose solution, and 10 µl each of blood was collected from the caudal vein after 0, 0.5, 1, 2, 3 and 4 hours to measure blood sugar level by the same method as described above. Further, 10 µl of blood collected in the same manner was mixed with 10 µl of heparin-containing physiological saline and centrifuged, and then the insulin level in the supernatant was quantified by using an enzyme immunoassay kit (Morinaga Milk Industry Co., Ltd, Biochemical Research Laboratory). The blood sugar levels and the insulin levels are shown in FIGS. 11 and 12, respectively. In FIGS. 11 and 12, the values are average values, and the bars represent standard deviations.

As shown in FIG. 11, the fasting blood sugar levels of the N-KO mice were significantly lower than those of the wt mice, and the blood sugar levels changed within a significantly low value range even after glucose was administered. It was considered that the 9- to 10-month old Wt mice had age-related insulin resistance, whereas changes in the blood sugar levels of the N-KO mice were similar to those of young mice.

This difference was also shown in the insulin levels shown in FIG. 12, and the Wt mice maintained a high insulin concentration before and after the glucose administration, whereas the N-KO mouse showed a low insulin concentration, which returned to the level before the glucose administration after 1 hour. Further, the insulin levels of the Wt mice significantly varied depending on each individual.

These experimental results indicate that the N-KO mouse does not become insulin resistant easily, and N-type Ca channel is involved in insulin resistance and further indicate that activation of the N-type Ca channel is associated with normalization of blood sugar level.

Amounts of glucagon and leptin were also measured, but no difference was observed between the Wt mice and the N-KO mice.

3. Immunofluorescence Staining of Spleen

In order to further confirm the involvement of N-type Ca channel in insulin resistance, pancreatic β cells in islets of Langerhans of a Wt mouse and an N-KO mouse were compared.

A Wt mouse and an N-KO mouse (male, 11-month old) were anesthetized with Nembutal and subjected to abdominal section, then a portion around a valve of the right atrium was excised, and blood was removed. PBS containing heparin (4 U/ml) was injected from the left ventricle, and whitening of the liver was confirmed. Then, 4% paraformaldehyde dissolved in PBS was further injected. When rigor of each individual was confirmed, the pancreas was removed and fixed with 4% paraformaldehyde at 4° C. for 1 hour. Following the fixation, the pancreas was left overnight in PBS containing 30% sucrose at 4° C. and embedded in an OCT compound to prepare a thin section.

The thin section was stained by using a guinea pig anti-insulin serum (Linco Research) as primary antibodies and rhodamine-labeled anti-guinea pig IgG antibodies (Chemicon International) as secondary antibodies, and the β cells containing insulin were observed with a fluorescence microscope. Similarly, the thin section was stained by using rabbit anti-glucagon antibodies (Linco Research) and FITC-labeled anti-rabbit IgG antibodies (Organon Teknika), and the α cells containing glucagon were observed.

In the N-KO mouse, a cell aggregation of β cells was small, and an increase in the number of β cells with aging was not observed, which was observed in the Wt mouse. On the other hand, no difference was observed in α cells between the both mice.

It is considered that the wt mouse had age-related insulin resistance and insulin production in β cells was accelerated, while the N-KO mouse did not have insulin resistance.

Example 6

Autonomic Innervation of Atrial Muscle Contractile Force of N-KO Mouse

Autonomic innervation of atrial muscle contractile force of an N-KO mouse was examined. The atriums were isolated from mice (Wt mice and N-KO mice: n=5 each), and the contractile force and the action potential were simultaneously recorded by giving a direct muscle stimulus and a nerve stimulus from two of stimulators. As for stimulus conditions, the basal stimulus was given with a frequency of 2 Hz, a voltage just above the threshold and a pulse width of 1 msec. The nerve stimulus was given with a frequency of 200 Hz, a voltage 1.5 times as high as the basal stimulus and a pulse width of 0.1 msec. Four nerve stimuli per basal stimulus were given during a refractory period of the cardiac muscle, which lasted 15 seconds.

Figure 13:
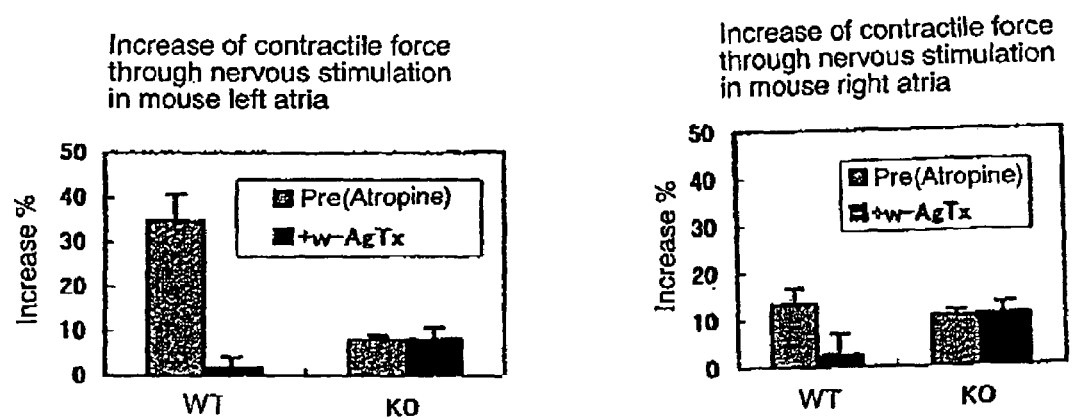
FIG. 13 shows comparison of autonomic innervation for atrial cardiac muscle contractile forces in an N-KO mouse and a wild-type mouse.

FIG. 13 shows experimental results in the left atrium and the right atrium of 5 cases. The values are average values, and the bars represent standard deviations. In the figure, w-CgTx represents ω-conotoxin GVIA.

In the left atrium, the atrial muscle contractile force of the Wt mouse was greatly increased by the nerve stimulus in the presence of atropine, and this increase in the contractile force was almost completely inhibited by 30 nM ω-conotoxin GVIA. On the other hand, although a slight increase was observed in the atrial muscle contractile force of the N-KO mouse by the nerve stimulus in the presence of atropine, this increase in the contractile force was not suppressed by the ω-conotoxin GVIA up to 100 nM. These increases in the contractile force were completely inhibited by 0.1 μM tetrodotoxin, although the data are not shown in the figure.

Although no increase in the contractile force of the atrial muscle caused by the atropine nerve stimulus was not so remarkable in the right atrial muscle as in the left atrium, the obtained result was almost similar to that of the left atrium.

These results are considered to suggest that the release of norepinephrine (NE) from the sympathetic nerve mostly depended on N-type Ca channel in the Wt mouse, but Ca channels of other types were increased in a compensatory manner and contributed to the release of NE in the N-KO mouse. In the Wt mouse, it is expected that an increase in the contractile force by a nerve stimulus in the right atrium is smaller than that in the left atrium and hence there is a difference in innervation densities in the left and right atriums.

INDUSTRIAL APPLICABILITY

The present invention provides an animal that does not show a functional expression of N-type Ca channel By using the animal of the present invention, the function of the N-type Ca channel can be deduced. Further, by administrating a drug to an N-KO animal and a wt animal, whether the drug acts on the N-type Ca channel can be deduced from the difference in their responses. Furthermore, there are provided a method for screening for a substance having a pharmacological action on blood pressure control, transmission of pain, blood sugar level control and so forth by using the animal of the present invention, a substance having a pharmacological action obtained by the screening method and a method for manufacturing a drug comprising screening for a substance having a pharmacological action by the screening method and manufacturing a drug comprising the obtained substance as an active ingredient.

What is claimed is:

1. A transgenic mouse in which a gene coding for the $\alpha_{1B}$ subunit of the N-type calcium channel is disrupted so that the mouse lacks the functional $\alpha_{1B}$ subunit of the N-type calcium channel, wherein said disruption results in an increased heart rate and blood pressure, decreased transmission of second phase pain or decreased insulin and glucose levels after feeding.

2. The transgenic mouse according to claim 1, wherein the gene comprises DNA defined in the following (a) or (b):
   (a) DNA which comprises the nucleotide sequence of SEQ ID NO: 1;
   (b) DNA which hybridizes with DNA comprising the nucleotide sequence of SEQ ID NO: 1 under a stringent condition of hybridization at 65° C. in 4×SSC and subsequent washing at 65° C. in 0.1×SSC for 1 hour and codes for the functional $\alpha_{1B}$ subunit of the N-type calcium channel.

3. A method for screening for a substance having a pharmacological action, which comprises a step of determining pharmacological action of the substance by the method of (a) or (b):
   (a) a method which comprises steps of administering a substance to the transgenic mouse as defined in claim 1 and determining the pharmacological action of the substance, or
   (b) a method which comprises steps of administering a substance to the transgenic mouse as defined in claim 1 and a wild-type mouse, and comparing the pharmacological actions of the substance on the transgenic mouse and the wild-type mouse to determine the pharmacological action of the substance, wherein the pharmacological action is an action for lowering blood pressure, an analgesic action, or an action for lowering blood sugar level.

4. A method for manufacturing a pharmaceutical composition, which comprises steps of screening for a substance having a pharmacological action by the method as defined in claim 3 to obtain a substance having an action for lowering blood pressure an analgesic action, or an action for lowering blood sugar level, and mixing the obtained substance with a pharmaceutically acceptable carrier to manufacture a pharmaceutical composition comprising the obtained substance as an active ingredient.

5. The method according to claim 3, wherein the pharmacological action is an action for lowering blood pressure.

6. The method according to claim 3, wherein the pharmacological action is an analgesic action.

7. The method according to claim 3, wherein the pharmacological action is an action for lowering blood sugar level.

* * * * *

UNITED STATES PATENT AND TRADEMARK OFFICE
CERTIFICATE OF CORRECTION

| | |
|---|---|
| PATENT NO. | : 7,067,714 B1 |
| APPLICATION NO. | : 10/111827 |
| DATED | : June 27, 2006 |
| INVENTOR(S) | : Ino et al. |

It is certified that error appears in the above-identified patent and that said Letters Patent is hereby corrected as shown below:

On the front page of the patent under Assignee, delete "Eisai Research Institute" and insert --Eisai Co., Ltd.--.

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,067,714 B1 | Page 1 of 1 |
| APPLICATION NO. | : 10/111827 | |
| DATED | : June 27, 2006 | |
| INVENTOR(S) | : Ino et al. | |

It is certified that error appears in the above-identified patent and that said Letters Patent is hereby corrected as shown below:

Item (73)
On the front page of the patent under Assignee, delete "Eisai Research Institute" and insert --Eisai Co., Ltd.--.

In the title, item (54), delete "N-CALCIUM" and insert -- N-TYPE CALCIUM --;

In the Foreign Application Priority Data, Item (30), insert

-- Feb. 16, 2000    (JP) ............................... 2000-37839
       Aug. 31, 2000    (JP) ............................... 2000-261979 --

In claim number 4 (column 48, line 24), delete "pressure an analgesic" and insert -- pressure, an analgesic --.

Signed and Sealed this

Twenty-fourth Day of October, 2006

JON W. DUDAS
*Director of the United States Patent and Trademark Office*